United States Patent
Bond et al.

[11] Patent Number: 6,161,435
[45] Date of Patent: Dec. 19, 2000

[54] METHOD AND APPARATUS FOR DETERMINING THE STATE OF FOULING/CLEANING OF MEMBRANE MODULES

[75] Inventors: Leonard J. Bond, Richmond, Wash.; Guo Yong Chai, Boulder, Colo.; Alan Richard Greenberg, Boulder, Colo.; William Bernard Krantz, Boulder, Colo.

[73] Assignee: University Technology Corporation, Boulder, Colo.

[21] Appl. No.: 09/358,733

[22] Filed: Jul. 21, 1999

Related U.S. Application Data

[60] Provisional application No. 60/093,615, Jul. 21, 1998.
[51] Int. Cl.⁷ .............................. G01D 7/00; B01D 17/06; B01D 33/00
[52] U.S. Cl. .............................. 73/587; 210/748; 210/785
[58] Field of Search .............................. 73/587, 579, 602, 73/596, 597, 598, 599, 600, 614, 615, 616, 620, 625, 627, 628, 629; 210/748, 785, 650, 651, 791, 411, 412, 413, 414

[56] References Cited

U.S. PATENT DOCUMENTS

| | | | |
|---|---|---|---|
| 4,253,962 | 3/1981 | Thompson | 210/414 |
| 4,728,368 | 3/1988 | Pedziwiatr | 134/184 |
| 5,298,161 | 3/1994 | Sieg | 210/321.78 |
| 5,919,376 | 7/1999 | Carman | 210/785 |

*Primary Examiner*—Helen C. Kwok
*Attorney, Agent, or Firm*—E. Hancock; F. A. Sirr; Holland & Hart LLP

[57] ABSTRACT

The fouling state of a polymeric membrane within the high pressure housing of a spiral wound or a hollow fiber membrane module is determined. An ultra sonic transducer positioned with its emitting face in physical engagement with the outer surface of the housing is pulse energized by a pulser/receiver device. A membrane echo signal is detected by a receiver of the pulser/receiver device. A reference echo signal indicative of a fouled or an unfouled state of the membrane is compared to the echo signal to determine the membrane fouling state. The echo to reference comparing step can be based upon comparing amplitude domain signals, comparing time-domain signals, comparing combinations of amplitude domain and time-domain signals, and comparing transformations of amplitude domain and time-domain signals. A clean or a fouled reference echo can be provided from a clean or a fouled membrane and then stored for use during a liquid separation process, or a clean reference echo signal can be obtained on-line from a second transducer whose echo signal is derived from an area of the membrane known to remain relatively unfouled during the liquid separation process, or a clean or fouled reference echo signal can be provided for later use during a cleaning process or during a liquid separation process. Multiple transducers and a switching network can sample the fouling state at different positions within the membrane module.

50 Claims, 9 Drawing Sheets

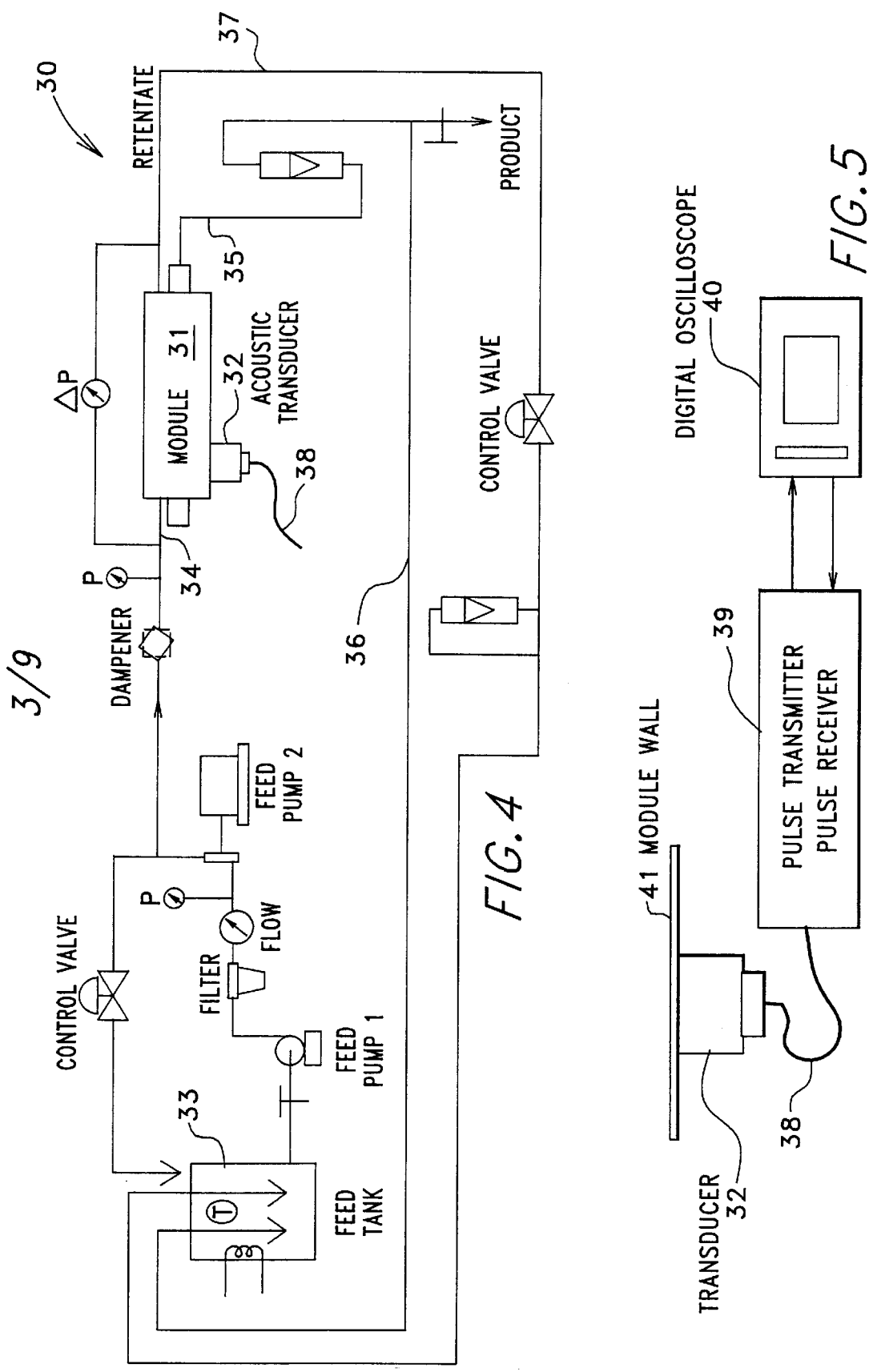

METHOD AND APPARATUS FOR DETERMINING THE STATE OF FOULING/CLEANING OF MEMBRANE MODULES

CROSS-REFERENCE TO RELATED APPLICATION

This nonprovisional application claims the benefit of prior filed and copending provisional application number 60/093,615 filed Jul. 21, 1998 by Leonard Bond and Guo-Young Chai and entitled FOULING METER FOR SPIRAL WOUND AND HOLLOW FIBER MEMBRANE MODULES.

BACKGROUND OF THE INVENTION

1. Field of the Invention

This invention relates to the field of liquid separation processes that use membrane systems, and more specifically, to methods and apparatus for determining the state of fouling and/or the state of cleaning of such membrane systems.

2. Description of Related Art

It is known that ultrasonic transducers can be used with ultrasonic pulser/receiver equipment to provide a wide variety of ultrasonic test systems, with emphasis on high-frequency applications, examples being high-resolution flaw detection, thin material thickness gaging, medical research, and materials characterization to measure sound velocity and attenuation, which in turn can be correlated to elastic modulus or grain orientation (size/texture).

The use of membranes in water treatment applications is known, and a joint NWRI/NSF workshop panel has recognized the importance of detecting and monitoring the fouling process with the development of non-destructive, on-line, real-time observation techniques (AWWA Membrane Technology Research Committee, JAWWA, 84(1), 59, (1992)).

The measurement of inorganic fouling using sensor technology based upon acoustic Time Domain Reflectometry (TDR) has been reported in the *Review of Progress in Quantitative NDE* (*Nondestructive Evaluation*), 14, 1167, 1995, and other work has indicated the feasibility of utilizing acoustic TDR for measurement of biofouling, Report to the Bureau of Reclamation, Mar. 26, 1996.

Measurement of the fouling and/or cleaning of membranes that are used in liquid separation processes is pivotal to the art if membranes are to be widely used. The lack of suitable techniques for studying membrane fouling under realistic operating conditions has hindered the development of strategies to improve resistance to fouling. Moreover, although a decline in the permeate flow rate (i.e., the treated liquid flow rate) can be used to infer that membrane fouling is occurring, or has occurred, flow rate measurement does not provide a determination of when a membrane module has been adequately cleaned via chemical means, back flushing, or any other cleaning means, since permeation flow does not occur during membrane cleaning, and flow rate measurements are not made during cleaning.

It is known that the fouling of membrane modules can be detected by means of an optical probe. However, use of an optical probe requires that an optical window be formed in a wall of the housing that internally holds the membrane. This procedure is not practical in commercial high-pressure membrane modules. Moreover, optical probes provide information on membrane fouling relative to only on the outermost portion of the membrane. That is, interior membrane portions cannot be seen via an optical probe.

It is also known that an indirect measurement of membrane fouling can be obtained via measurement of the permeate flow rate out of the membrane, an increase in back pressure, or via measurements of the output permeate's composition. Membrane fouling is known to cause a decline in the permeate flow rate. However, permeate flow rates can decline for reasons other than membrane fouling. For example, concentration polarization and membrane compaction also causes the permeate flow rate to decline. Moreover, permeate flow rate measurements cannot be used to assess the effectiveness of cleaning fouled membrane surfaces, since normal permeate flow measurement does not occur during membrane cleaning.

The same criticisms apply to using an analysis of the permeate composition to assess membrane fouling. In particular, permeate composition does not provide appropriate information during the cleaning of fouled membrane modules, since feed composition changes occur during cleaning.

Membrane fouling has been identified as the major factor that limits the implementation of membranes in liquid separation processes. Moreover, membrane fouling limits the time period during which a membrane module can be used before a need to clean the membrane module arises.

It is known that others have used ultrasonic time-domain reflectometry when studying membrane formation and membrane processes. This prior work has involved studies of membrane formation, membrane compaction, membrane fouling, and defect formation in membranes. However, this aforementioned work has not included an apparatus, meter or method for measuring membrane fouling and/or membrane cleaning in membrane modules, such as spiral wound and hollow fiber membrane modules. For example, see an article entitled Real-Time Nondestructive Characterization of Membrane Compaction and Fouling, REVIEW OF PROGRESS IN QUANTITATIVE NONDESTRUCTIVE TESTING, Vol. 14, Plenum Press, 1995, pages 1167–1173, that describes how compaction and fouling were characterized in-situ, and in real-time, using a nondestructive ultrasonic technique relative to a thin film membrane whose structure consisted of a 0.2 micro-meter thick polyamide layer supported by a 40 micro-meter thick polysulfone substrate attached to a 150 micro-meter thick polyester web.

A description of spiral wound membrane modules and hollow fiber membrane modules, as will be discussed in the following detailed description of the present invention, can be found in the publication MEMBRANE HANDBOOK by W. S. Winston and K. K. Sirkar, Van Nostrand Reinhold, 1992.

The present invention satisfies a need in the art for an apparatus/method for detecting the initiation of membrane fouling as well as the state of membrane fouling and the rate of membrane fouling, to thereby provide an early warning that permits adjusting system operating parameters to mitigate the fouling problem.

By providing a measurement of membrane fouling, the present invention satisfies a need in the art for an apparatus/method that determines when a membrane module should be cleaned, as contrasted to techniques that provide measurements that might be a result of factors other than membrane fouling, such as membrane compaction.

This present invention also satisfies a need in the art for an apparatus/method that permits determining when a membrane module has been adequately cleaned via chemical or any other cleaning means. As such, the present invention satisfies a need in the art for an apparatus/method for reducing the amount of cleaning chemicals or other cleaning agents that are required for membrane cleaning, thus also minimizing the down time that is required to clean membrane modules.

The present invention also satisfies a need in the art for an apparatus/method that can be used with membrane modules that are used in a wide range of liquid separation tasks, such as water desalination and reclamation, and the processing of feed streams and waste liquid feed streams.

In general, there is a need in the art for a fouling meter/method that operates to monitor membrane module fouling and/or membrane cleaning, in a non-destructive manner, on-line, in real-time, and non-invasively.

SUMMARY OF THE INVENTION

The present invention provides a fouling meter that operates to monitor membrane fouling and/or membrane cleaning within a membrane module, online, in real time, and noninvasively.

An example of the utility of this invention is with membrane modules (i.e., a unitary assembly having a membrane that is contained within a rigid, high pressure, metal, plastic, or metal/plastic composite housing) that are used in the treatment of water or other liquids, wherein a flux flow, product flow, or permeate flow decline, results from fouling of the membrane, as is caused by inorganic contaminants, and/or organic contaminants, and/or biological contaminants in the membrane module's input water, feed water or liquid feed.

In addition, the present invention finds utility when a fouled membrane is cleaned, for example, but without limitation thereto, by passing a chemical cleaning solution through the membrane module, by back-flushing, or when the membrane module is cleaned by any such means.

The present invention employs ultrasonic or Acoustic Time-Domain Reflectometry (ATDR) to detect membrane fouling noninvasively, in real-time, and the invention operates to detect membrane fouling on an internal portion or portions of a membrane that is housed within a rigid metal, plastic, or metal/plastic housing. Moreover, this invention does not require that any type of window be cut in the housing to permit detecting the fouling of a membrane that is within a membrane housing. This invention also distinguishes between membrane fouling and changes that might result from concentration polarization or membrane compaction.

A particular advantage of this invention is that the apparatus/method of the invention can be used to assess the degree of membrane fouling during cleaning of the membrane, and therefore the invention can be used to terminate the costly cleaning process when operation of the invention determines that a membrane module has been satisfactorily cleaned.

ATDR has been successfully applied to measure the location of physical interfaces. ATDR is based upon the principle that the time (t) that is taken by sound to travel a distance (d) is shown by the formula $t=2d/c$, where c is the velocity of sound through the medium. The intensity of sound that is echoed, or reflected, from a target surface depends on the nature of the target surface. If a sound source is directed toward the target surface, the position and the amplitude of a target echo peak in the time domain depend upon the roughness or topography of the target surface, depend upon the distance of the target surface from the sound source, and depend upon the acoustic impedance of the target surface, where the acoustic impedance is equal the product of p and c, where p is the density of the target surface material, and where c is the speed of sound in the target surface material.

A typical ATDR scheme whereby an interface between a liquid and a solid or semi-solid 12 is monitored by an acoustic transducer 13 is shown in FIG. 1. The time domain/amplitude (hereinafter amplitude-domain) response of such an interface to an energy pulse from transducer 13 is an echo signal as shown in FIG. 2.

A feed solution 14 enters FIG. 1 arrangement under pressure, and occupies an open area 15 that is defined by the lower surface 16 of an upper or top structural (for example, metal or a polymer composition) plate 17, and by the upper surface 18 of material 12 that includes a membrane layer 19 and a contamination or fouling layer 20. A porous support layer 21 lies below membrane layer 21, a lower or bottom structural plate 22 is provided below support layer 21, and permeate flow 23 exits from support layer 21 as retentate flow 24 exits from area 15.

Transducer 13 directs an energy wave onto the upper surface 25 of top plate 17, and this energy wave is reflected by two interfaces; namely (1) an interface that is formed by the bottom surface 16 of top plate 17 and the top surface of the liquid that is within area 15, and (2) an interface that is formed by the bottom surface of the liquid that is within area 15 and the top surface 18 of the membrane layer/fouling layer area 12.

An echo or reflection signal is provided by both of these two interfaces. The time domain/amplitude domain response of these two interface reflections is shown in FIG. 2. The reflection or echo signal that is provided by the interface that is formed by the bottom surface 16 of top plate 17 and the top surface of the liquid that is within area 15 is shown at 26. As will be apparent to those of skill in the art, the time position and the amplitude of signal 26 does not change with operation of the FIG. 1 device. Thus, signal 26 can comprise a reference signal.

Assuming that the device of FIG. 1 contains no fouling layer 20, echo signal 27 of FIG. 2 originates at an interface that exists between the bottom surface of the liquid that is within area 15 and the top surface of membrane layer 19.

Now assume that membrane fouling occurs; i.e., that fouling layer 20 exists. As a result, a dotted line echo signal 28 is provided by the interface that is formed by the bottom surface of the liquid that is within area 15 and the top surface 18 of the membrane layer/fouling layer area 12.

Since the interface that is formed by the bottom surface of the liquid that is within area 15 and the top surface 18 of the membrane layer/fouling layer area 12 is physically closer to transducer 13 than was the above-discussed unfouled interface, echo 28 moves in the time domain to the left from echo 27 by a delta-t value that is equal to two times the FIG. 1 distance delta-s, divided by c, where c is the velocity of the sound that is generated by transducer 13 in the liquid that occupies area 15.

If the acoustic impedance contrast at the echo interface changes, then he amplitude or amplitude domain of echo 28 increases or decreases, depending upon the direction of the change in the acoustic impedance. Surface characteristics, such as roughness, also influence amplitude. For example, a specular reflection from an interface will produce a higher amplitude echo than does a scattered reflection from a rough interface.

The principles above described relative to FIGS. 1 and 2 are used in the operation of the present invention, wherein the fouling of a membrane operates to change both the distance between the membrane/solution interface and the transducer (the distance change depending upon the thickness of the fouling material) and the acoustic impedance of the membrane/solution interface. As an example, increased thickening of layer 12 causes echo pulse 27 to move to the left in FIG. 2, and compaction of membrane 19 causes echo pulse 27 to move to the right in FIG. 2. In some cases, membrane fouling will not result in an appreciable change in the distance between the membrane/solution interface and the transducer.

The present invention provides a unique in situ and noninvasive method/apparatus that quantifies the fouling of a spiral wound or a hollow fiber membrane, in real-time, using acoustic time domain reflectometry. This invention also has utility in determining membrane fouling/cleaning in membrane based liquid separation systems (i.e., microfiltration systems, ultrafiltration systems, nanofiltration systems, and reverse osmosis filtration systems).

A valuable utility of this invention provides a membrane fouling meter or device for the noninvasive and real time measurement of membrane fouling/cleaning. Such a fouling meter has utility in determining the optimal time for which a membrane module should be cleaned. Moreover, this fouling meter facilitates determining when the membrane module has been adequately cleaned. In addition, this fouling meter has utility in assessing the effectiveness of new techniques that are developed to control and mitigate membrane fouling.

This invention adapts the ATDR technology to the measurement of membrane fouling and membrane cleaning in membrane modules that employ multi-layer membrane elements, such as spiral wound and hollow fiber membrane elements.

The invention provides a basis for the use of on-line acoustic sensors that are suitable for the timely detection of fouling, as well as the use of on-line acoustic sensors to measure the efficiency of cleaning protocols that are used for commercial liquid separation systems.

Fouling of a membrane is generally defined as the deposition of retained particles, colloids, macromolecules, and/or salts on or within a membrane. Generally, a permeate flux decline accompanies fouling in membrane separations, including, but not limited to, microfiltration, ultrafiltration (UF), nanofiltration, and reverse osmosis (RO).

As used herein, the term spiral wound membrane means a structure wherein a membrane sandwich, such as two flat sheet membranes that are separated by a flat sheet porous channel spacer member, is wound about a centrally-located product water or permeate collection tube, to thereby assume a convenient cylindrical form that is then placed into a hollow, cylindrical shaped, outer housing member. Prior to winding, three sides of the membrane sandwich are glued together, and the fourth side is glued into the product water collection tube. A feed water stream is passed into one end of the cylindrical module and along one side of the wound membrane sandwich. This feed water permeates the membrane and passes into the channel spacer member as product water. The product water travels in a spiral, until it reaches the center or longitudinal axis of the module. There, the product water flows through small holes that are formed in the product water collection tube, whereupon the water exits the module through a product water outlet. Retentate that does not permeate the membrane exits the module through an outlet at the opposite end of the module. Generally, in a spiral wound membrane, the individual layers of the spiral-wound membrane do not experience the same magnitude of liquid pressure or pressure differential.

As used herein, the term hollow fiber module means a structure wherein a relatively large number of elongated, small diameter, and hollow membrane tubes are packed into a cylindrically shaped, high pressure, housing, such that the elongated central cavity of all tubes extending in a common direction from one end of the housing to the other. A feed water stream is passed into the housing and along the outer cylindrical surfaces of all tubes. This feed water permeates the membrane tubes. Product water then travels through the center of all membrane tubes, until it reaches one end of the housing. There, the product water exits the housing through a product water outlet. Retentate that does not permeate the membrane tubes exits the housing module through a retentate outlet that is located at this other end of the housing. In general, all membrane tubes experience the same magnitude of liquid pressure or pressure differential.

In operation, a liquid to be treated (for example, sea water), enters the membrane module by way of a liquid inlet. This liquid is under a high pressure, such as 600 psi, or more generally in the range of about 200 to about 1,000 psi. This liquid then permeates, spreads, or diffuse through the module's internal membrane. The permeate exits the membrane module by way of a first liquid outlet, as the brine or retentate exits the module by way of a second liquid outlet. As will be appreciated, during this separation of the inlet liquid into an output permeate liquid and an output retentate liquid, residual material is left on the membrane, and in this manner, the membrane becomes fouled during use. Also as will be appreciated, the highest concentration of impurities, such as salt, occurs adjacent to the above-mentioned second liquid outlet, i.e. the retentate outlet.

This invention relates to the use of an ATDR technology to measure membrane fouling, and to measure the efficiency of membrane cleaning, in Reverse Osmosis (RO) membrane module system employing both spiral wound and hollow fiber membranes, one example being a RO system that used Filmed SW30-2521 spiral-wound membrane modules, and another example being a hollow fiber membrane module by Akzo-Nobel.

By way of example, but without limitation thereto, a 3 MHz pulse mode energized, 4-inch focal length, 1-inch diameter, ATDR transducer can be used to observe 1-mm diameter hollow fibers in hollow fiber membranes or in spiral-wound membranes, wherein the membrane module includes a circular cylinder external housing with an outer diameter of about 3-inches and an axial length of about 18-inches. A frequency range of usable transducer energization extends from about 0.5 to about 5 MHz. The low frequency end of such a range is selected to provide good penetration of the ultrasonic energy through the membrane module. The high frequency end of such a range is selected to provide an echo signal having good resolution. With the two considerations of penetration and resolution in mind, a transducer energization frequency of about 3 MHz was selected.

In perfecting this invention, a bench scale RO system, as shown in FIGS. 4 and 5, was provided to obtain reproducible data, and a protocol was developed in order to carry out controlled fouling experiments with membrane modules 31 containing spiral wound membranes. The parameters of the ATDR transducer 32 were determined in order to achieve a desired measurement resolution. Studies of both clean and systematically fouled membrane modules 31 were performed using an ATDR system to obtain on-line measurements.

RO system 30 was constructed and arranged so as to obtain independent control over the liquid pressure and liquid flow rate for the membrane module 31 being tested. As a result, the ATDR system provided for the measurement of inorganic fouling and cleaning in real-time relative to commercial membrane modules 31.

With reference to FIG. 4, feed liquid was provided to membrane module 31 from tank 33 by way of a pipe 34. Permeate exited membrane module 31 by way of a pipe 35, and at least a portion of the permeate was recycled to tank 33 by way of a pipe 36. Retentate exited membrane module 31 by way of a pipe 37 and was recycled to tank 33.

As best shown in FIG. 5, transducer 32 was physically mounted onto the exterior surface 41 of the membrane module's outer housing wall using a suitable coupling agent to facilitate transmission of the acoustic signal into the module, and an electrical conductor 38 connected transducer 32 to an ultrasonic pulse transmitter/pulse receiver or pulser/receiver 39 that, in turn, provided a signal to an oscilloscope 40 on which a signal such as shown in FIG. 9 was visually provided.

In the development of this invention, a replication of calcium sulfate fouling and cleaning studies using spiral-wound membrane modules supplied by Fluid Systems were performed wherein A-scan and B-scan measurements were made along the axis of the spiral-wound membrane in order to assess module geometric and flow effects on membrane fouling. The ATDR signals from each successive spiral-wound membrane layer were isolated, or a complete response from many membrane layers was used, and a determination was made relative to the influence of system operating parameters including pressure on ATDR measurements.

In an embodiment of this invention, ATDR studies of membrane fouling and membrane cleaning efficiency were made using #2521 spiral-wound membrane modules supplied by Filmtec. Typical operating conditions were 225 psi, 22 C, feed concentration of 820 mg/l of $CaSO_4$, and a running time of approximately 95 hours. FIG. 9 shows an ATDR signal trace that was obtained during the cleaning of a spiral-wound membrane module.

A-Scan (point) measurements were carried out at several positions along the axis of the spiral-wound membrane module. The ATDR measurements suggested that the propensity of the membrane to foul increased in the direction of flow. This is consistent with the concentration boundary layer being thicker in the downstream direction, thereby causing increased concentration polarization.

With reference again to FIG. 4, data accumulated indicated that a decline in the rate of permeate flow 35 was reasonably correlated with a change in the amplitude of echo signal 38. In addition, there was a corresponding decrease in the arrival time of echo signal 38. The effects of changes in the operating parameters of system 30 on the amplitude of echo signal 38 indicated that only changes in the pressure within pipe 34 upstream of membrane module 31 and changes in the temperature of the liquid within pipe 34 significantly affect the amplitude of echo signal 38. It was also determined that an increase in temperature also resulted in a systematic decrease in the arrival time of echo signal 38.

More specifically, with temperature and flow rate held constant, as input pressure increased a decrease in the amplitude of echo signal 38 was observed, and with input pressure and flow rate held constant, as temperature increased an increase in the amplitude of echo signal 38 was observed.

An initial ultrasonic transducer design included two acoustic transducers by Panametrics having about a 3 MHz energizing frequency, about a 1-inch diameter, and a focal length of from about 3 to about 4-inches. In order to accurately interpret the ATDR signals, it is helpful, but not necessary, to know the velocity of sound within the various materials used in the membrane modules being tested.

By determining the geometrical parameters and materials of construction of the membrane modules, more information can be extracted from the acoustic ATDR signals, such as, but not limited to, determining the reflections or echoes from each successive membrane layer.

When one uses the ATDR technique of this invention to study how fouling varies along the axis of the membrane module, a behavior is observed wherein fouling increases in the direction of feed flow presumably due to an increased concentration polarization.

While this invention provides that this unique ATDR technique can be used to perform inorganic fouling studies, this technique is also useful relative to studying organic fouling and/or biological fouling.

Unique advantages of this invention include:

Quantitative Data: Current techniques permit determining membrane fouling only via indirect measurements of quantities, such as the permeation flow rate. Flow rate can change due to factors other than membrane fouling; for example, concentration polarization and membrane compaction. Permeate flow rate provides only a measure of the permeate flux integrated throughout the entire module rather than being a local measurement; whereas fouling can be a localized phenomenon owing to the influence of module hydrodynamics that vary along the module. Moreover, permeate flow rate can be measured only when a module is in operation; as such, flow rate provides no information during membrane cleaning. The present invention, employing ultrasonic time domain reflectometry, provides local measurement of membrane fouling. As such, the invention can be used to scan across the bulk of a membrane module, to thereby permit improved module design and/or module operating conditions. This apparatus/method of this invention can also be used at any time that the module is liquid filled. Hence, this invention can be used to provide information on membrane fouling both during operation and during cleaning.

Simplicity: The present invention utilizes an ultrasound technology, the elements of which have been successfully applied to both nondestructive testing and a wide range of process measurement applications. This invention provides a simple technique for the direct measurement of membrane fouling. By comparing the reflection or echo signal (or the complete response from a series of membrane layers) that results from operation of this invention, either during operation or during cleaning, with a calibration reflection signal that defines a clean membrane, it is possible to assess both the presence of, and the degree of, membrane fouling. An embodiment of this invention employs transducers that are fixed in position and do not require mechanical scanning.

Ease of Application: This invention can be retrofitted onto many current membrane modules, and can also be integrated into newly-manufactured membrane modules. The invention does not require a housing window to access the interior of the membrane module. An embodiment of the invention employs a stand-alone unit that can be removed from one membrane module, and installed on another membrane module.

Versatility: This invention can be applied to modules having either a spiral-wound or a hollow fiber membrane, as well as to other types of membranes. This invention operates to detect the presence of membrane fouling that occurs due to suspended particulates, as well as inorganic, organic, and biological precipitates.

Image Data: A modified form of this invention employs scanning to thereby image local membrane fouling that may be localized within the bulk of a membrane, in contrast to other techniques that only provide data relative to the entire membrane.

These and other advantages and features of the invention will become apparent to those of skill in the art upon reference to the following detailed description, which description makes reference to the drawing.

BRIEF DESCRIPTION OF THE DRAWINGS

FIG. 4 provides a showing of bench scale RO system that was used to obtain reproducible data, and with which a protocol was developed in order to carry out controlled fouling experiments with membrane modules containing spiral-wound membranes.

FIG. 5 shows the transducer portion of the FIG. 4 arrangement in greater detail.

DESCRIPTION OF PREFERRED EMBODIMENTS

Figure 1:
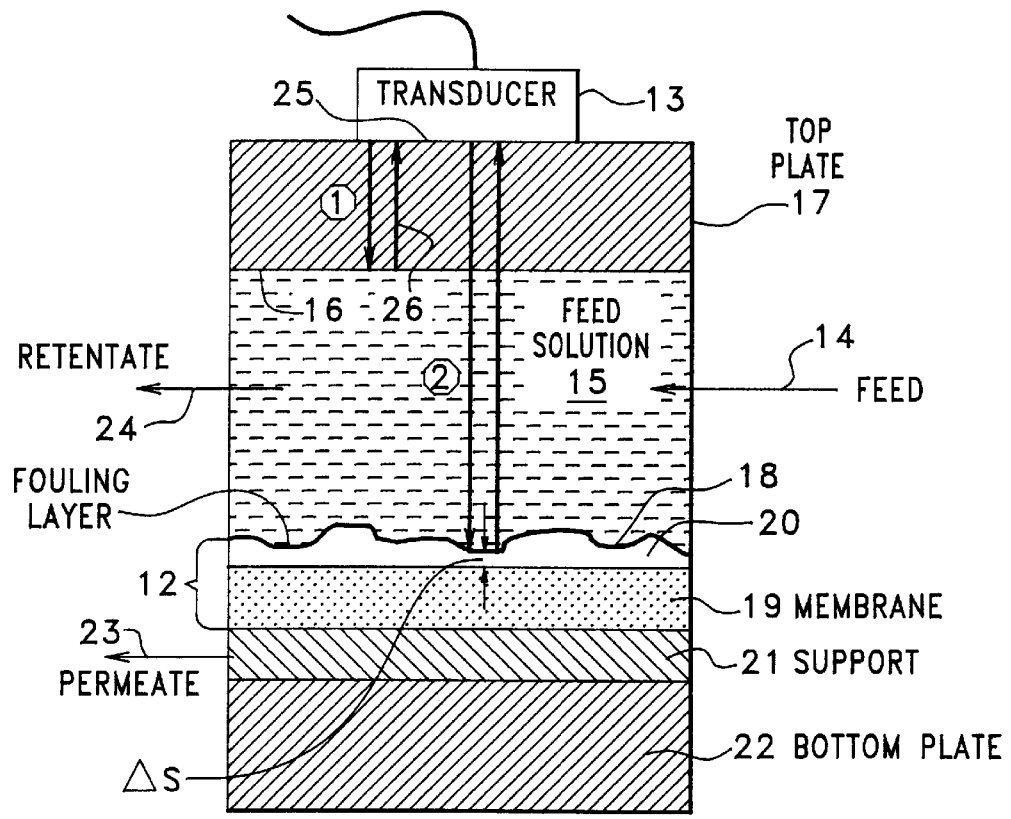
FIG. 1 shows an arrangement for using ATDR to monitor a liquid/solid interface or a liquid/solid like interface.
Figure 2:
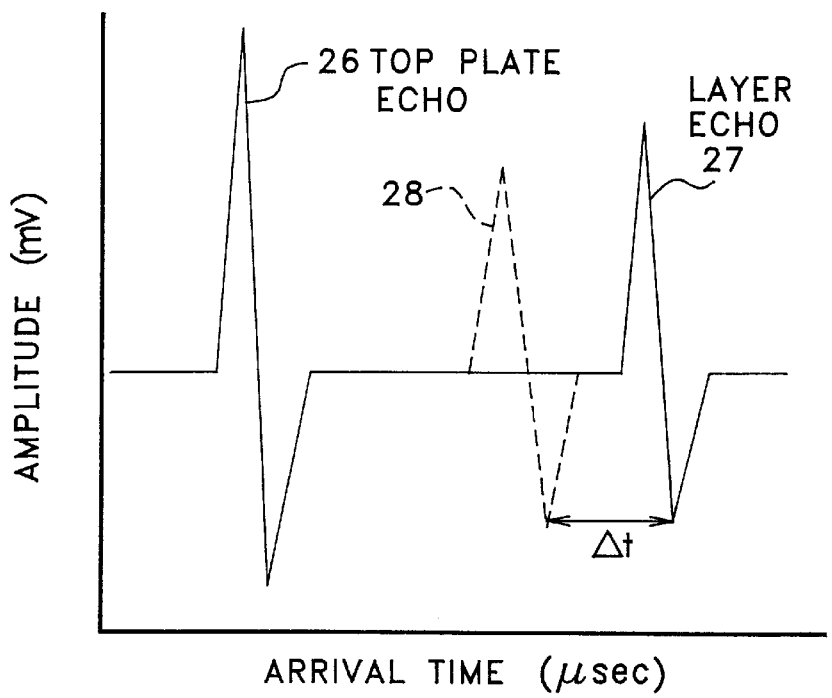
FIG. 2 shows various types of echo pulses that can be derived from the arrangement of FIG. 1.

One aspect of the present invention provides an apparatus/method for measuring the fouling of pressure driven membrane modules; for example, membrane modules that contain either a spiral-wound membrane or a plurality of hollow fiber membranes. The invention provides for a measurement of the buildup of particulates and/or precipitates on a membrane that is contained within the housing of a membrane module. In a new and unusual manner, this invention employs an ultrasonic measurement system that employs high frequency sound waves to detect the presence of membrane fouling/cleaning in a noninvasive and real-time manner.

The invention employs either a single ultrasonic transducer, two ultrasonic transducers, or an array of ultrasonic transducers, to obtain data about the localized state of fouling/cleaning that exists at a location(s) that is buried within the bulk of the membrane that is contained within the membrane module's housing.

The ultrasonic transducer preferably comprises a focused transducer that operates to emit ultrasonic energy that is focused at a known distance beyond the energy emitting face of the transducer. The transducer may include a flat emitting face, that matches a flat area that is provided on the module external housing, or it may include an emitting face that is curved to match the curve of the module external housing. The transducer is mounted with its emitting face abutting the outside surface of a hollow structural tube (for example, an aluminum tube) that comprises the housing of the membrane module. Preferably, a compliant acoustic couplant material is placed between the transducer's emitting face and the external surface of the membrane module.

The transducer is now pulse energized, to preferably produce a transmit-receive or pulse echo mode of operation. A time-domain membrane reflection or echo signal or multilayer response is recorded. Comparison of this reflection signal to a standard or reference enables a determination to be made as to the state of membrane fouling/cleaning.

In one embodiment of the invention, the reflection standard comprises an echo signal that is obtained from a transducer prior to actual use of the associated membrane module, which echo signal is then stored for later use.

In another embodiment of the invention, the reflection standard comprises the on-line output of a second pulse echo energized transducer that is located to interrogate the membrane at a location at which it is known that the membrane remains relatively unfouled during operation. Such a location may be adjacent to the membrane module liquid or feed inlet. In this manner, the refection standard signal provides on-line compensation for operating parameters, such as liquid temperature.

In another embodiment of the invention, the reflection standard signal comprises a clean membrane reference signal that is supplied by the module manufacturer, based upon prior testing of the particular type of membrane module.

In an embodiment of the invention, a number of transducers are located along the axial length of the membrane module (for example, between the liquid inlet and the permeate outlet), to thereby better monitor the state of fouling/cleaning of the entire membrane.

In yet another embodiment of the invention, a transducer is movable along the axial length of the membrane module; for example, between the liquid inlet and the permeate outlet.

Figure 6:
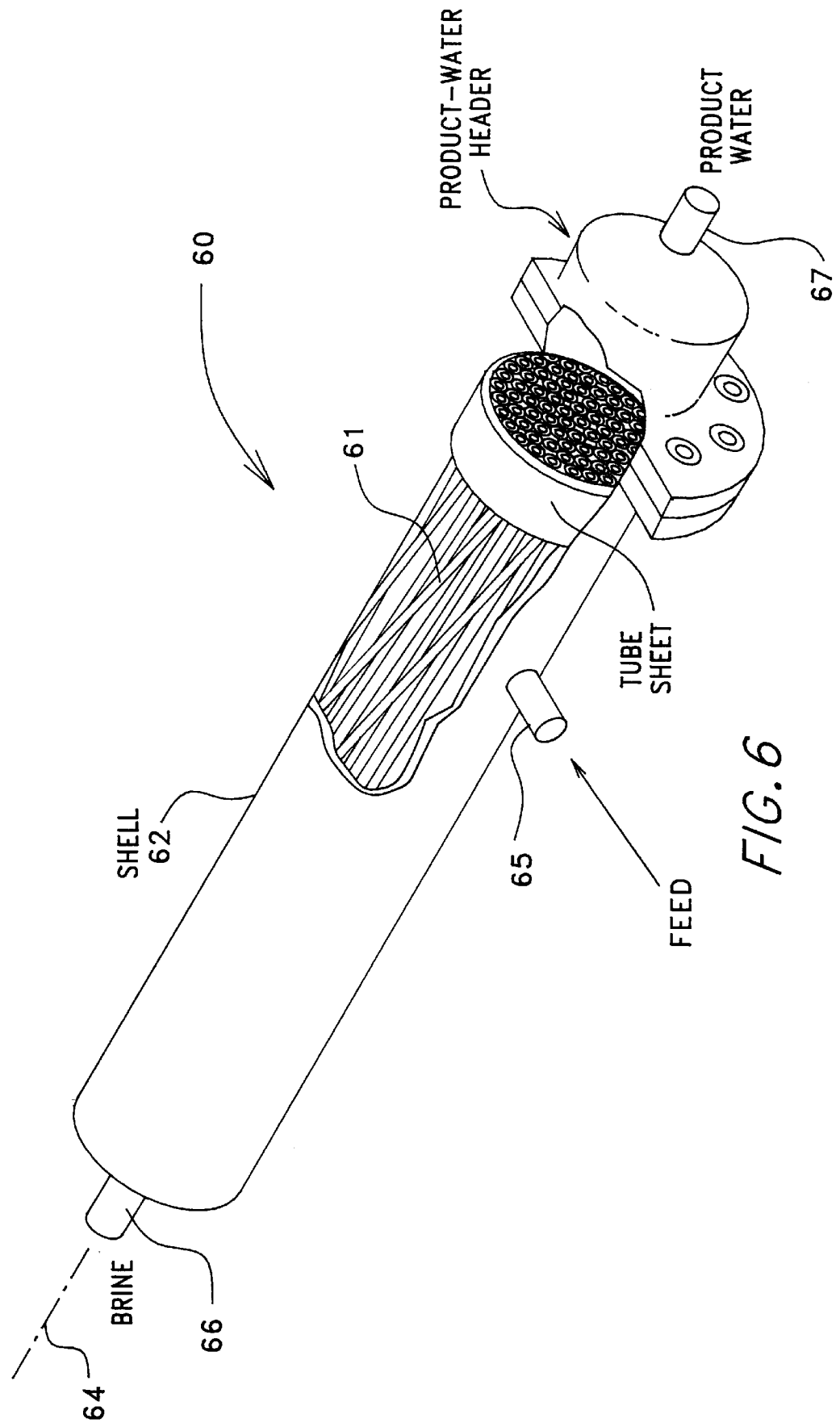
FIG. 6 provides a partially broken away showing of a hollow fiber membrane module having an outer high pressure and cylindrical housing that contains a relatively large number of generally parallel and hollow membrane tubes that are sealed or potted at each end so that liquid feed flows into one end of the housing, as permeate liquid exits the center volume of the membrane tubes and is collected at a permeate output.
Figure 16:
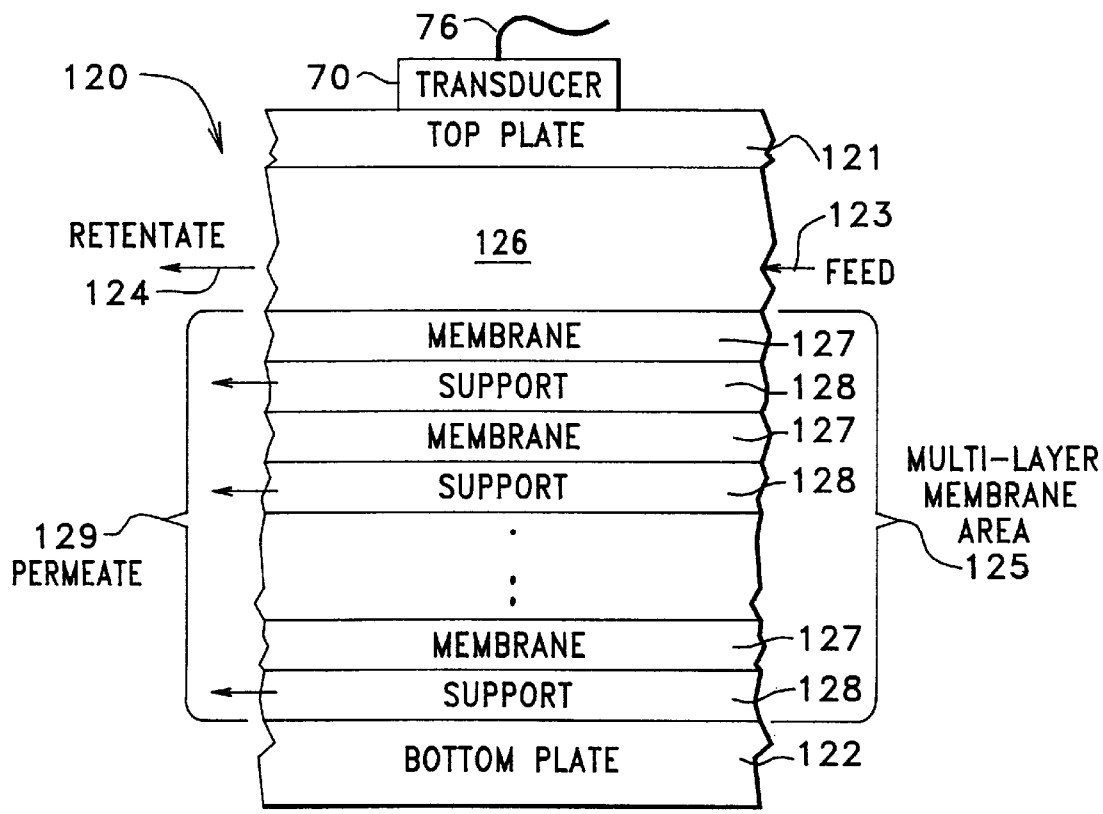
FIG. 16 shows another type of multiple-reflecting-layer membrane module with which the present invention finds utility.

The apparatus/method of this invention provides an electrical, on-line, output that informs the user of the module fouling/cleaning condition. While the invention will be described relative to spiral-wound and hollow fiber membrane that are contained within a generally circular cylinder external housing, such as is shown in FIGS. 3 and 6, the invention can be used with membranes and membrane modules having other configurations, such as is shown in FIGS. 1 and 16.

Figure 3:
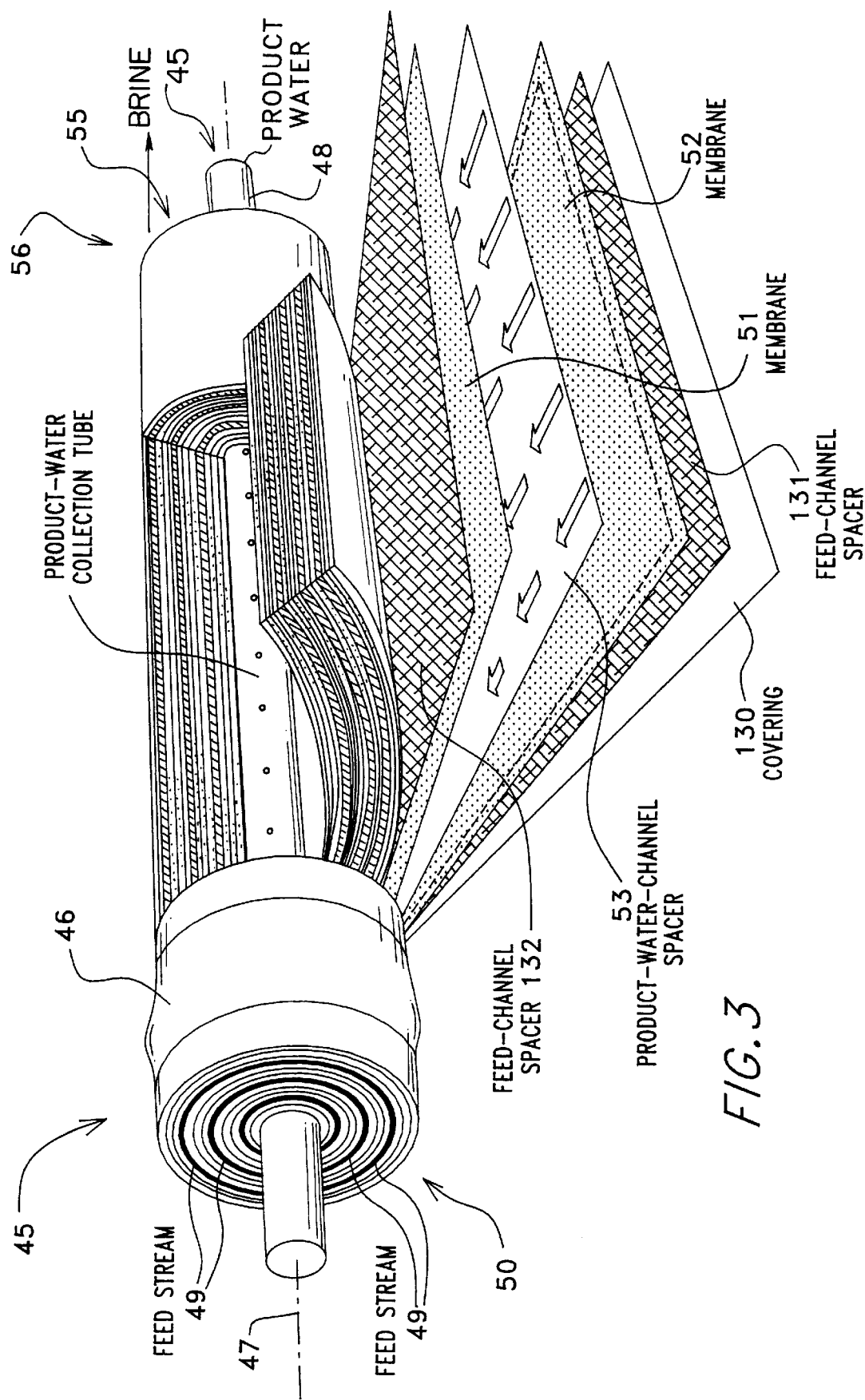
FIG. 3 provides a schematic showing of a spiral-wound membrane module having an outer high-pressure housing that contains a membrane that is made of a spiral wrapping having alternating layers of membrane material and spacer material, with a portion of the spiral wrapping being unwrapped to show its layer construction.

FIG. 3 provides a schematic showing of a conventional spiral-wound membrane module 45. Membrane module 45 includes a high-pressure outer housing 46 in the shape of a cylinder having a circular cross-section, a centrally-located axis 47, and a centrally located liquid or water collection pipe 48. An input feed stream 49, here assumed to be salt water, is supplied to the end 50 of membrane module 45.

For purposes of explanation, a portion of a spiral-wound membrane that is contained within membrane module 45 is shown as being unwound such that the various layers can be viewed.

Internally, module 45 includes a spiral-wound membrane sandwich that includes, in sequence, a covering sheet 130, a porous feed channel spacer sheet 131, a first membrane sheet 52, a porous permeate product water spacer sheet 53, a second membrane sheet 51, and a feed channel spacer sheet 51.

This membrane sandwich is wound about a centrally-located product water or permeate collection tube 48, to thereby assume a cylindrical form that is then placed into the hollow, cylindrical shaped, and outer housing member 46. Prior to winding, three sides the membrane sandwich are glued together, and the fourth side is glued into product water collection tube 48. A feed water stream 49 is passed into one end 46 of module 45, and along the one side of the wound membrane sandwich that is adjacent to end 46. This feed water stream 49 permeates membrane sheets 51 and 52, and passes into product water channel spacer member 53 as product water. The product water travels in a spiral until it reaches the center or longitudinal axis 47 of module 45. There, the product water flows through small holes (not shown) that are formed in product water collection tube 48, whereupon the water exits module at 45 through a product water outlet. Retentate, for example brine, that does not permeate membrane 51, 52 exits module 45 at 55 through an outlet (not shown) that is provided at the opposite end 56 of module 45.

As stated above, during operation of membrane module 45 to separate a liquid into a permeate and a retentate, the membrane area at the feed in end 50 of module 45 usually remains relatively free of contaminants, but only as compared to the membrane area at the retentate out end 56 of module 45.

FIG. 6 provides a showing of a conventional hollow fiber membrane module 60 that is made up of a large number of generally parallel and hollow fiber membrane tubes 61 that are placed into a rigid and tubular module housing or shell 63 having a central axis 64 and a generally circular cross-section. In the manner explained above, feed water under high pressure enters membrane module 60 at inlet 65, and in the case of treating salt water, brine exits membrane module 60 at retentate outlet 66. As the water passes over the exterior surfaces of the many hollow fiber membrane tubes 61, salt-free water fills the central void of each membrane tube. This salt-free water now flows to a second module outlet; i.e., permeate or product outlet 67.

Typical membranes of the above types involve complex geometries, generally involving a large number of curved surfaces that are formed by several different materials. This invention provides for a deconvoluting of the various reflection signals, or echo waves, that are generated by this complex membrane geometry.

In accordance with this invention, one, two, or more ultrasonic transducers are placed on the outside of a filtration/separation membrane module as shown in FIGS. 3 and 6, wherein the membrane module includes an outer high strength tube that is formed of a material, such as a plastic, a metal or a metal/plastic composite, in which either a spiral-wound membrane or a hollow fiber membrane is contained.

Within the spirit and scope of this invention the one or more ultrasonic transducers can be integrated onto the outer surface and/or into the inner surface of the module outer high pressure structural housing during the manufacture of the membrane module, and in a way so as to not compromise the high pressure strength of the housing.

Preferred, but without limitation thereto, the invention uses ultrasonic transducers that operate in a pulse echo mode. In accordance with the spirit and scope of this invention, one or more pairs of ultrasonic transducers that operate in the pitch-catch mode can also be used.

A pulsed electrical signal is converted into a mechanical signal within such an ultrasonic transducer, and in this manner, a series of ultrasonic energy pulses is sent into the interior of the membrane module. In the pulse echo mode of operation, the ultrasonic pulses are reflected back to the sending ultrasonic transducer from any interface that exists between different materials, at which interface there is a change in acoustic impedance; such a change being a product of material density and ultrasonic pulse velocity. A known device to operate with an ultrasonic transducer in the pulse echo mode is a device known as an ultrasonic pulser receiver, such as the Model 5052PR family of devices by Panametrics.

The ultrasonic transducer now converts these reflected signals, reflected pressure pulses, reflected pressure waves, or echo waves into electrical signals that comprise time-versus-amplitude traces having a complex waveform. The reflected time-versus-amplitude electrical signals are then automatically analyzed in order to provide a quantitative measurement of any fouling of the membrane, or to provide a quantitative measurement of the state of cleaning of the membrane that is within the membrane module.

Fouling of the membrane surface(s) results in changes in the amplitude and/or the arrival time of the reflection signals that are provided by the membrane. Considering the membrane layers that are near the outside surface of a spiral-wound module, and therefore closest to the ultrasonic transducer, in general the reflected amplitude increases as hard fouling occurs, such as might be caused by precipitation of inorganic salts. Both hard fouling and soft fouling, as might be caused by deposition of organic or biological materials, result in a decrease in the arrival time of the reflected signal.

The amplitude and/or the arrival time of the reflected signals that are received from membrane layers that are deeper within the membrane also change as membrane fouling develops. The nature of the amplitude/arrival time change is dependent upon the reflection and scattering that occurs at the membrane layers that are closer to the ultrasonic transducer. Also, the characteristics of the fouling signal that is received from each physical zone or layer that is within the bulk of the membrane through which the ultrasonic energy has passed changes for each such zone.

In applying the present invention to a particular type of membrane module and to particular membrane fouling conditions, calibration or reference data are obtained in order to permit the characteristics of clean and fouled membrane surfaces to be distinguished, one from the other. In this way, the invention provides a measure of the presence or absence of membrane fouling.

The invention is sensitive to inorganic fouling, such as due to the inorganic salts involved in desalination via reverse osmosis, biofouling such as is involved in use of membranes for water treatment, and particulate fouling such as result from deposition of suspended particles in a feed stream to a membrane module. The invention can be used both to detect fouling in membrane modules in real-time, as it occurs, and/or to detect the real-time removal of fouling deposits during the cleaning of membrane modules.

One embodiment of the invention (see FIG. 5 for example) includes one, or more, ultrasonic transducers, an ultrasonic pulser receiver, and a digital oscilloscope. Another embodiment of the invention (see FIG. 10 for example) includes one, or more, ultrasonic transducers, an ultrasonic pulse receiver, and a measuring means that automatically compares a reflection signal to a standard signal that is representative of a clean membrane. In an embodiment of the invention (see FIG. 12 for example), this standard reference signal is derived from an ultrasonic transducer that is associated with an input feed portion of the membrane module whereat the least amount of fouling occurs. In this manner, compensation for variable liquid parameters, such as liquid temperature, is obtained, in addition to providing a standard or reference signal.

A fouling meter in accordance with this invention includes one, or more, ultrasonic transducers and a comparison means (see FIG. 15 for example), or a signal processing means, that, when calibrated to a clean membrane standard, provides an output of a membrane fouling/cleaning condition. Such an output may be based upon a number scale that extends from 1 to 10, wherein increasing numbers correspond from clean to fouled for a particular membrane module system.

Figure 7:
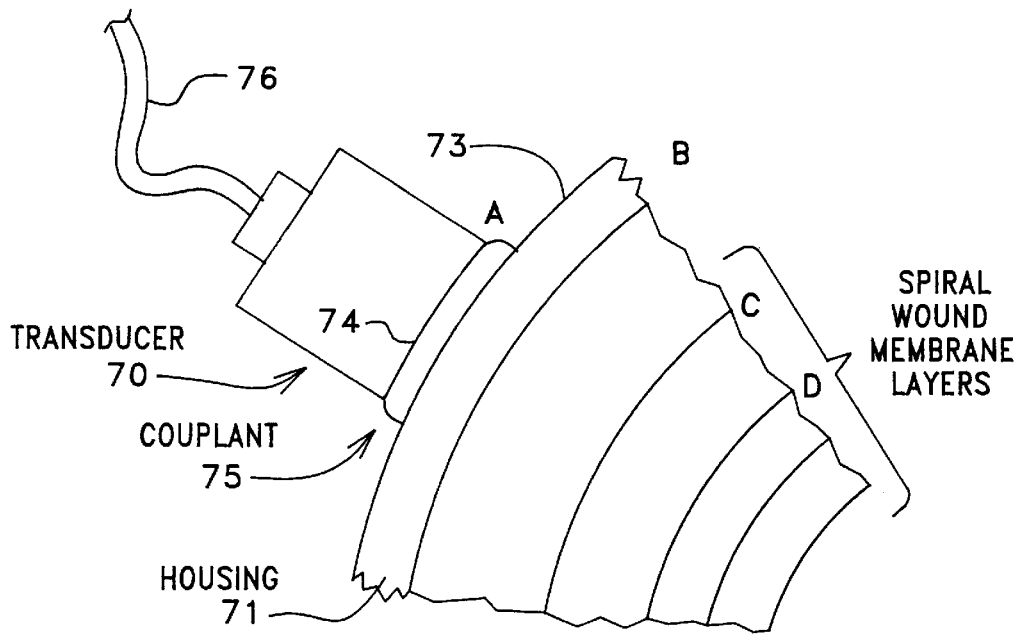
FIG. 7 shows an embodiment of the invention wherein an ultrasonic transducer is mounted on, or associated with, a portion of the external housing surface of a membrane module, for example, but without limitation to, the spiral-wound membrane module of FIG. 3, wherein the emitting face of the transducer is curved to physically match the curvature of the housing.

FIG. 7 is a partial end view of a membrane module showing an embodiment of the invention wherein an ultrasonic transducer 70 is mounted on, or associated with, a portion of the external housing surface 71 of a membrane module such as, but without limitation to, spiral-wound membrane module 45 of FIG. 3, or the hollow-fiber module 60 of FIG. 6. The letters A, B, C and D are associated with FIG. 7 to show the physical location of interfaces that contribute to correspondingly identified portions of the electrical signal shown in FIG. 9.

Figure 9:
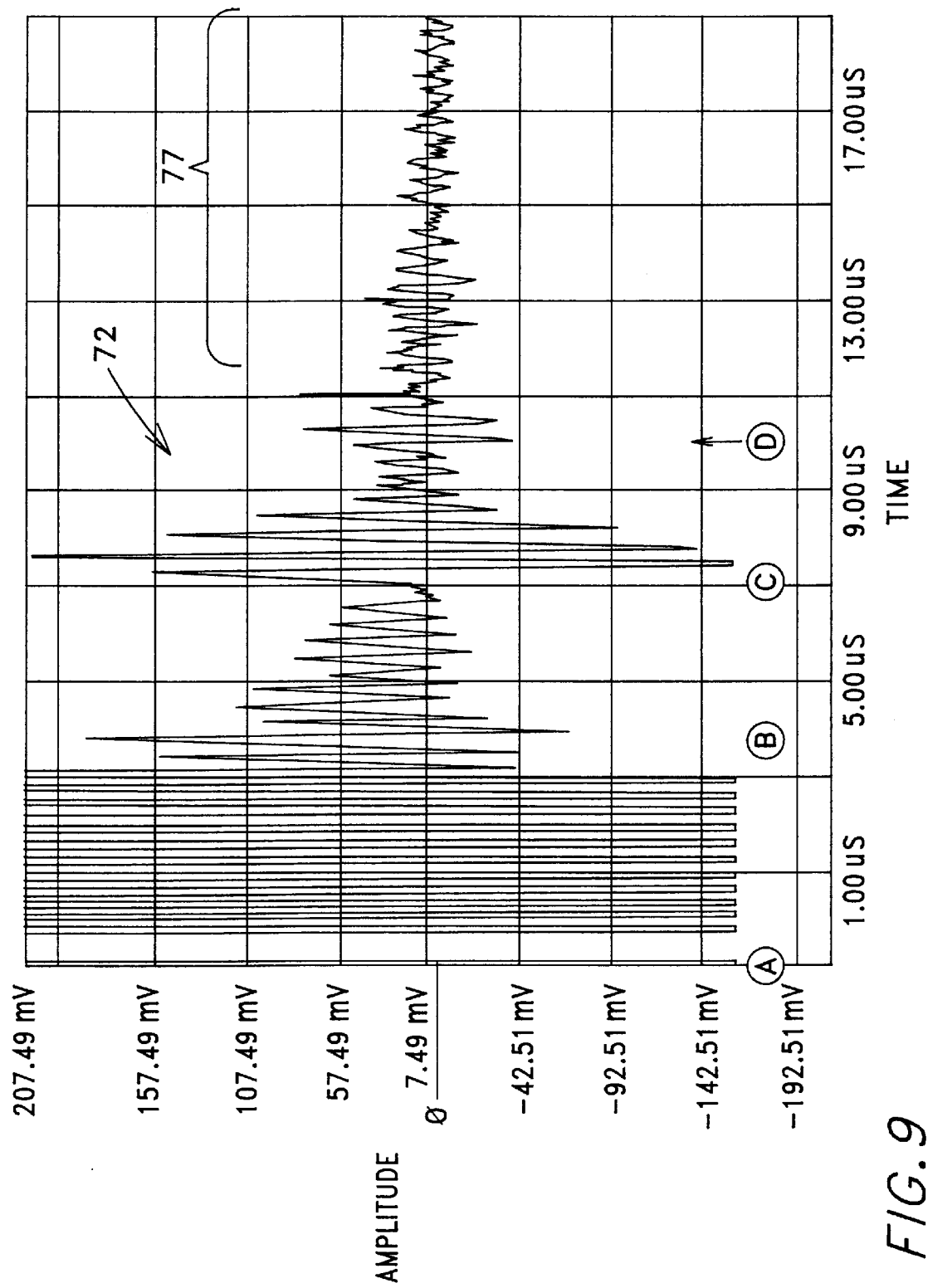
FIG. 9 is a time-versus-amplitude plot of an example electrical echo signal that is achieved by the pulse mode energization of the ultrasonic transducer of FIG. 7.

FIG. 9 is a time-versus-amplitude plot of a complex electrical echo signal 72 that is provided by transducer 70 when transducer 70 is pulse energized, wherein transducer 70 thereafter receives a plurality of acoustic echo waves that are reflected from the various interfaces A-D, and wherein transducer 70 responds to these echo waves and provides the electrical output signal 72 shown in FIG. 9, signal 72 containing signal portions A-D that correspond to FIG. 7 physical interfaces A-D.

As a feature of the invention, the exterior surface 73 of the housing is curved (for example, it is a portion of a cylinder as above described relative to FIGS. 3 and 6), and transducer 70 includes a curved energy emitting/receiving face 74 that is curved in a similar manner so as to match the curve of exterior surface 73. Preferably, a well-known acoustic couplant 75 is placed between transducer face 74 and surface 73, the thickness of couplant 75 being somewhat exaggerated in FIG. 7.

Pulse mode energization of transducer 70 produces a series of time-spaced energy waves that enter the membrane module. Each pulse energization of transducer 70, by way of multi-conductor cable 76, generates an energy wave that passes through couplant 75, through housing 71, and through the various membrane layers, including layers C and D that immediately underlie housing 71. As this energy wave hits an interface, a reflection or echo energy wave is produced, and these echo energy waves return and impact the face 74 of transducer 70. At transducer 70, an electrical signal is produced that is characteristic of the amplitude and the time of arrival of each individual echo wave. This electrical signal is provided as an output on cable 76.

FIG. 9 is an example of one such electrical signal 72, it being noted that such a signal 72 is generated by transducer 70 for each pulse energization thereof. The relatively high magnitude and initial portions A and B of signal 72 are of no interest relative to the state of fouling/cleaning of the membrane, since this echo energy is derived from couplant 75 and housing 71. However, the amplitude domain and/or the time domain of the next two portions C and D of signal 72 are indicative of the state of fouling of spiral wound membrane layers.

When the portions C and D, and perhaps the remaining portion 77, of electrical echo signal 72 are compared to an unfouled membrane or clean membrane electrical standard signal, an output is provided that is indicative of the state of fouling of the membrane module, or that is indicative of the state of cleaning of a fouled membrane. In an embodiment of the invention, but without limitation thereto, a signal mask was used to restrict this signal comparison to include a comparison to the low signal-to-noise ratio portion C of signal 72.

Figure 8:
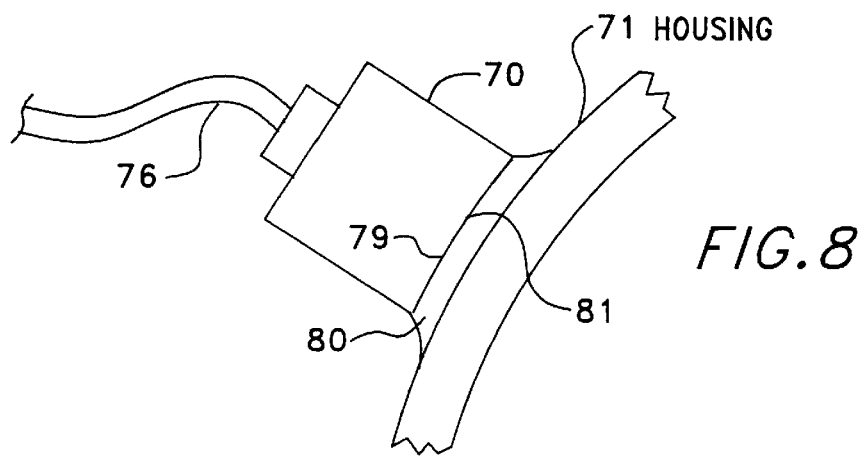
FIG. 8 shows an embodiment of the invention wherein an ultrasonic transducer is mounted on, or associated with, a portion of the external housing surface of a membrane module, and wherein the housing includes a protruding flat-top area that physically matches the flat emitting face of the transducer. An alternative to FIG. 8 (not shown) is to provide the external housing of a membrane module with a flat-top area that is machined into, or formed into, the cylindrical surface of the housing.

FIG. 8 is similar to FIG. 7 and shows an embodiment of the invention wherein ultrasonic transducer 70 of FIG. 7 is mounted on, or associated with, an extending portion 80 of the external housing 71 of the membrane module. In this embodiment of the invention, transducer 70 includes a flat surface pulse-emitting/pulse-receiving face 79, and the module's housing 71 has been shaped at 80 to include a matching flat surface area 81. Preferably, housing portion 80 is physically integral with housing 70, so as to avoid providing an additional echo interface. Flat surface area 81 physically matches the flat emitting/receiving face 79 of transducer 70. As is the usual practice, a couplant (not shown) is provided intermediate surfaces 79 and 81.

While the characteristics of the transducer to be used in the practice of this invention can vary over a reasonably wide range, it is preferred that a broadband, heavily damped, transducer that can be used with commercially-available ultrasonic Non-Destructive Testing (NDT) equipment be used in the practice of the invention. As a feature of the invention, the pulse-emitting/echo-receiving face of the transducer is curved to match the curved external surface of the membrane module whose internal membrane is being monitored.

An example of a usable transducer is the brand Videoscan Contact Transducer by Panametrics. Transducers of this type, when combined with broadband instrumentation, demonstrate performance characteristics that are necessary for the inspection of structures requiring maximum transducer damping, bandwidth, or resolution. Such transducers are known to provide good penetration in scattering or attenuating materials, and in flaw detection applications they demonstrate front surface and overall depth resolution, while maintaining sensitivity to locate deep-lying reflectors.

In a non-limiting embodiment of this invention, an ultrasonic transducer was used having about a 4.00-inch focal length and a transmitting/receiving surface or face was about 0.75-inch in diameter, wherein the transducer was pulse-mode energized with a frequency of about 3 MHz. Such a transducer was used to monitor the state of fouling or cleaning of a membrane module in the form of a cylinder having a circular cross section, whose outer diameter was about 3-inches and whose axial length was about 18-inches. Having a focused transducer whose focal length is somewhat greater that the diameter of the membrane module being monitored is desirable since a relatively reflection large area is provided at each membrane interface. While a focused transducer is preferred, use of such a transducer is not required since the cylindrical membrane module effects a focusing of the ultrasonic energy.

A transducer in accordance with this invention is used with instrumentation, such as a digital oscilloscope and an ultrasonic pulser/receiver, of which the brand Nicolet Pro digital oscilloscope and the brand Panametrics pulser/receiver are examples.

The pulser section of the pulser-receiver produces an electrical pulse that is applied to excite the ultrasonic, piezoelectric transducer. The transducer then operates to emit an ultrasonic pulse. In pulse echo applications such as the present invention, this ultrasonic pulse travels through the test material comprising the membrane module and its multi-layer membrane, and this pulse is reflected from the various membrane interfaces back to the transducer. The transducer receives the reflected pulses and converts the pulses into an electrical signal, which signal is then amplified and conditioned by the receiver section of the pulser/receiver, whereupon the amplified/conditioned signal is made available for automatic or visual analysis, including using a personal computer and analysis software.

Through transmission applications are much the same, but in this case, the ultrasonic pulse travels through the test material to a second transducer that acts as a receiver.

Figure 10:
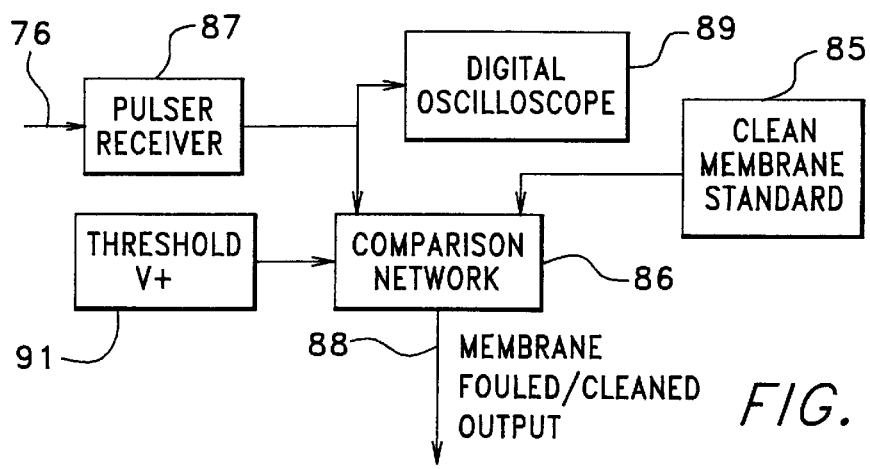
FIG. 10 shows an embodiment of the invention wherein a clean membrane reference signal is provided by first viewing, or interrogating, a clean or unfouled membrane, and then storing this clean membrane signal for later use in comparison to a transducer signal, such as is shown in FIG. 9.

In an embodiment of the invention shown in FIG. 10, the above-mentioned clean membrane or unfouled membrane electrical standard signal 50 is provided by using the arrangement of FIG. 7 or FIG. 8 to view, or interrogate, a clean or unfouled membrane that is within a membrane module. The resulting electrical signal 72 of FIG. 9 that is thus derived from transducer 70 and the clean membrane signal is then stored and used as the above-mentioned clean membrane electrical standard signal 85.

In the alternative, the arrangement of FIG. 7 or FIG. 8 can be used to view, or interrogate, a fouled membrane that is within a membrane module, in which case, the resulting electrical signal 72 of FIG. 9 that is derived from transducer 70 and the fouled membrane is stored and used as the above-mentioned fouled membrane electrical standard signal 85.

Reference signal 85 is presented as one input to a comparison network 86 wherein the time domain and/or the amplitude domain of signal 85 is compared to the time domain and/or the amplitude domain of an echo signal 76 that is provided by transducer 70 and pulser/receiver network 87 when transducer 70 views, or interrogates, a membrane module that is currently being used to process a liquid, or when transducer 70 views or interrogates a membrane module that has been fouled and is currently being cleaned.

In either event, when a time-domain comparison threshold and/or amplitude domain comparison threshold, and/or frequency domain comparison threshold that is provided by network 86 is met relative to signals 85 and 76, an output 88 is provided, indicating that the membrane module that is being used to process a liquid is beginning to foul and should be cleaned, or indication that a membrane module that is being cleaned has been sufficiently cleaned, whereupon the costly cleaning process is terminated. In addition, if desired, a digital oscilloscope 89 may be added to enable visual inspection of the sensing output 90 of pulser/receiver 87.

Figure 11:
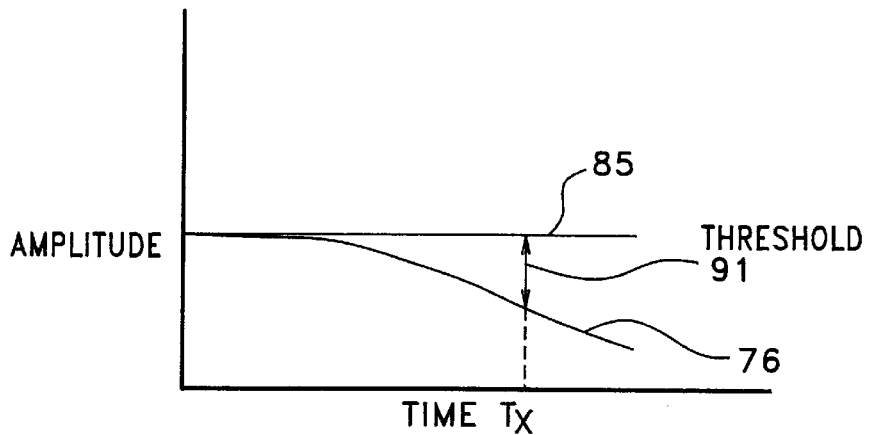
FIG. 11 shows a simplified example of the operation of FIG. 10 wherein the unfouled membrane reference signal is shown as having a generally flat response with time, wherein the echo signal that is provided by a transducer that interrogates a membrane module currently in use reduces in magnitude with time, and wherein at time Tx a threshold is met, and an output indicates that the membrane module should be cleaned.

FIG. 11 shows a simplified example of the operation of FIG. 10 wherein an unfouled reference membrane signal 85 is shown as having a generally flat response with time, wherein the signal 76 that is provided by transducer 70 interrogating the membrane module reduces in magnitude with time, and wherein at time Tx threshold 91 is met, whereupon output 88 indicates that the membrane module should be cleaned. Again, it should be noted that signals 76 and 85 of FIG. 11 are simplified showings of two corresponding portions of two much more complex signals of the type shown in FIG. 9.

Figure 12:
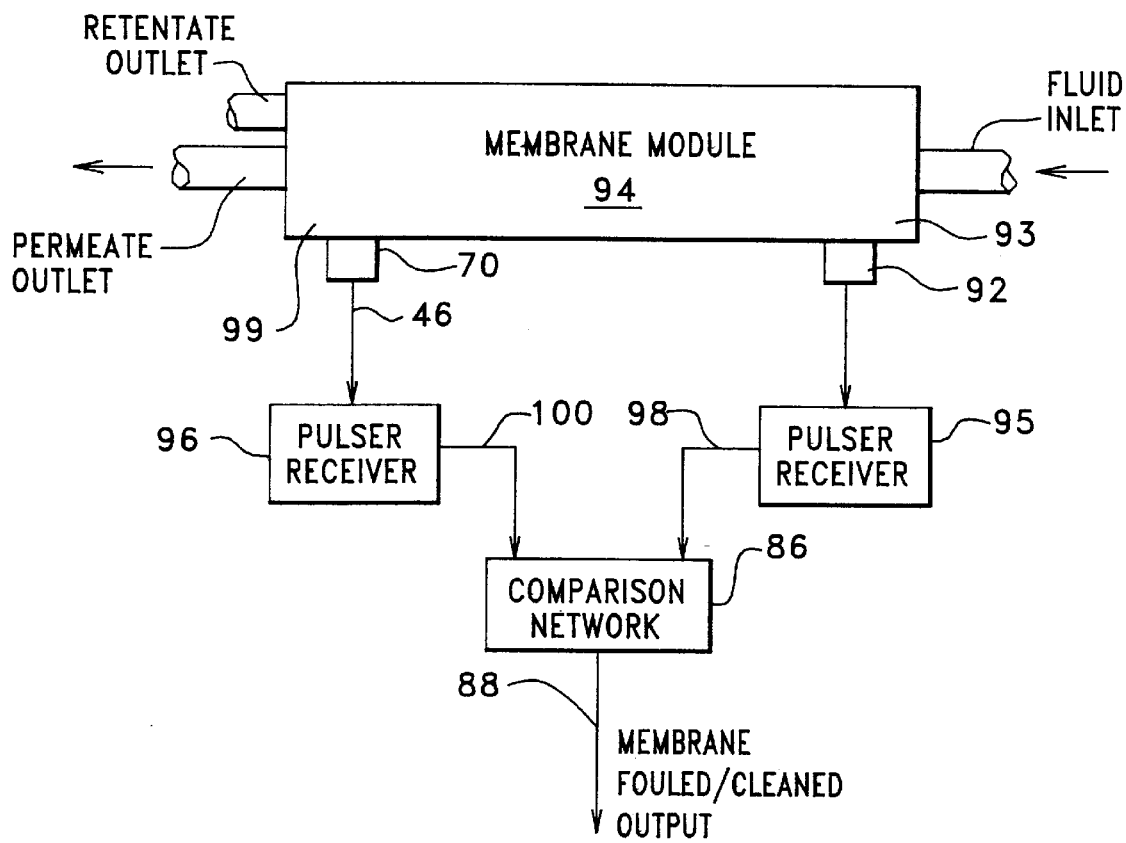
FIG. 12 shows an embodiment of the invention wherein a pseudo-unfouled membrane reference signal is provided by a second or reference ultrasonic transducer that is positioned in the manner of FIG. 7 to view, or interrogate, a portion of a membrane module; for example, the liquid inlet portion of a membrane module, whereat it is known that the membrane remains relatively unfouled during use. While two pulser-receivers are shown in FIG. 12, it is within the spirit and scope of the invention to provide a single pulser-receiver that operates with both the sensing transducer and the reference transducer.

In the FIG. 12 embodiment of the invention, the above-mentioned clean membrane electrical standard signal is provided by a second or reference ultrasonic transducer 92 that is positioned in the manner of FIGS. 7 and 8 to view, or interrogate, the fluid inlet portion 93 of a membrane module, such as 94. In FIG. 12, both the reference transducer 92 and the sensing transducer 70 are preferably operated in the pulse echo mode by the respective operation of pulser/receiver 95 and pulse receiver 96. As above noted, a single pulser/receiver can be provided if desired.

In this FIG. 12 embodiment, the liquid inlet portion 93 of the membrane that is within membrane module 94 provides a pseudo clean membrane standard signal 98 due to the fact that this portion of the membrane is known to experience a minimum of fouling, whereas the retentate or liquid outlet portion 99 of the membrane generally experiences a maximum of fouling, and provides a signal 100 that is indicative of the actual and current state of fouling, or the actual and current state of cleaning, of the membrane that is contained internal of membrane module 94.

In this case, comparison network 86 operates to compare the time-domain and/or the amplitude domain of reference signal 98 to the time-domain and/or the amplitude domain of fouled state signal 100. When a predefined relationship, as defined by comparison network 86, is found to exist between the two signals 98 and 100, output 88 indicates that membrane module 94 should be cleaned, or the costly cleaning of membrane module 94 can be terminated.

Figure 13:
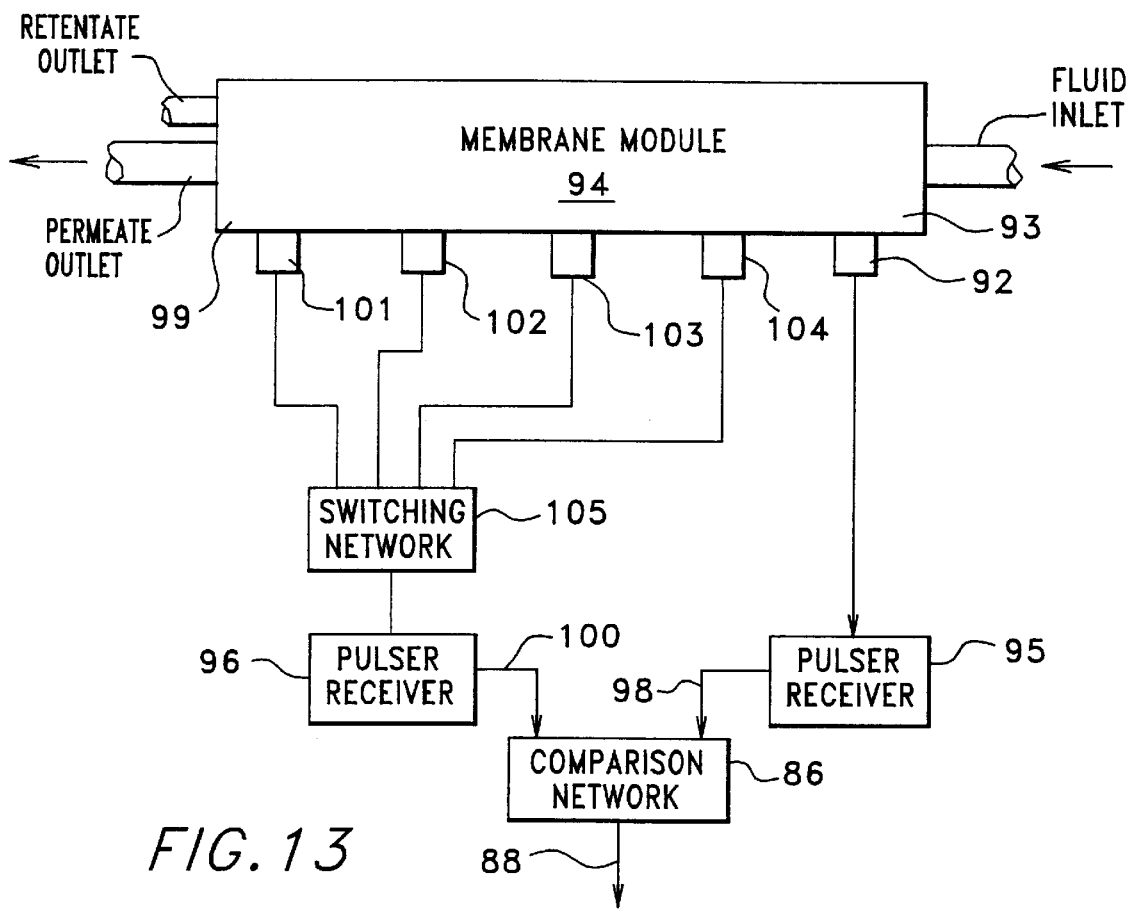
FIG. 13 shows an embodiment of the invention that is somewhat similar to the FIG. 12 embodiment, a difference being that four sensing transducers are provided in the FIG. 13 embodiment, and a switching network operates to sequentially connect one of the four transducers to cooperate with an ultrasonic pulser/receiver network. While two pulser-receivers are shown in FIG. 13, it is within the spirit and scope of the invention to provide a single pulser-receiver that operates with both the switching network and the reference transducer.

FIG. 13 shows an embodiment of the invention that is somewhat similar to the FIG. 12 embodiment, a difference being that four sensing transducers 101, 102, 103, and 104 are provided in the FIG. 13 embodiment. In this embodiment, a switching network 105 is provided to sequentially connect one of the four transducers 101–104 to cooperate with pulser/receiver network 96. In this embodiment, the clean membrane or unfouled membrane reference signal 85 can be provided as is above discussed relative to FIG. 10 and signal storage means 85, or, as shown in FIG. 13, the clean membrane reference signal 98 can be provided in the manner above described relative to FIG. 12 relative to the operation of reference transducer 92 and reference pulser/receiver 95.

FIG. 13 operates to generate an output signal 88 when the membrane that is internal of membrane module 94 becomes fouled at any one of the four locations that are being periodically viewed, or interrogated, by the four sensing transducers 101–104 and sensing pulser/receiver 96. It is also within the spirit and scope of this invention to generate output signal 88 when a preselected number of the four sensing transducers 101–104 provide an output echo signal that indicates fouling at the corresponding membrane locations.

In the case of cleaning membrane module 94, it is best, but not required, that signal 88 be generated only when all of the four membrane locations that are being interrogated by the four sensing transducers 101–104 have become cleaned by operation of a cleaning process.

Figure 14:
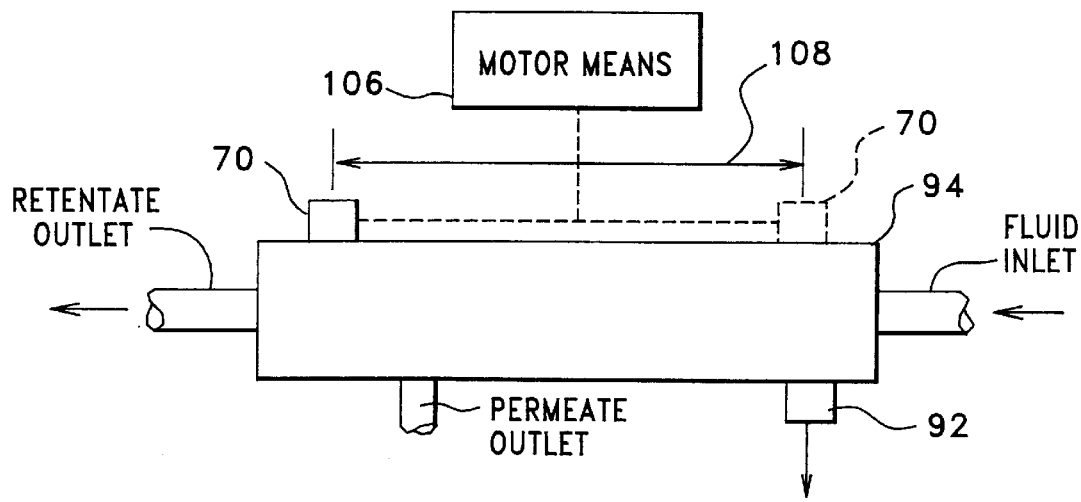
FIG. 14 shows another embodiment of the invention that operates in the manner of FIG. 13, a difference being that a drive motor means operates to physically move a single ultrasonic transducer, either in steps or continuously, so as to cause the transducer to interrogate a length of the membrane that is contained internal of the membrane module.

FIG. 14 shows another embodiment of the invention that operates in the manner of FIG. 13. However, in this case, a motor means 106 is operated to move sensing transducer 70, either in steps or continuously, so as to cause sensing transducer 70 to interrogate a portion of the length 109 of the membrane that is contained internal of membrane module 94.

Figure 15:
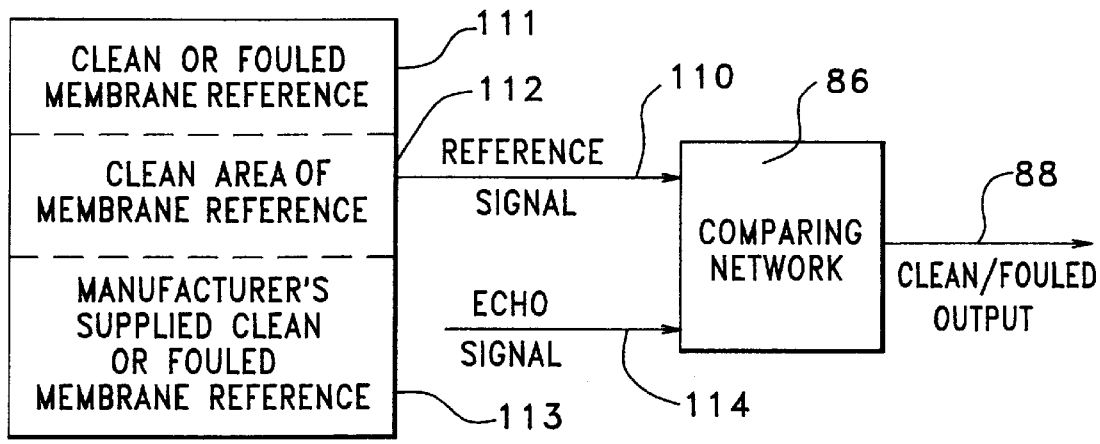
FIG. 15 shows how a reference signal can be provided alternatively by a clean membrane reference signal, by a clean membrane area reference signal, or by a reference signal that is supplied with a module, the reference signal of any type being for comparing to an echo signal that is provided by a transducer. such as is shown in FIGS. 7 and 8.

FIG. 15 is provided to show alternate means whereby a clean membrane reference signal, an unfouled membrane reference signal, or a fouled membrane reference signal can be provided at 110 as an input to comparison network 86.

As shown in FIG. 15, signal 110 can be provided by (1) a stored clean membrane reference signal 111 or a stored fouled membrane reference signal 110 that is generated by the arrangement of FIG. 10, or by a means that is equivalent thereto, (2) a clean membrane area reference signal 112 that is generated by the arrangement of FIG. 12, or by a means that is equivalent thereto, or (3) a manufacture supplied clean membrane reference signal 113 or fouled membrane reference signal 113 that is supplied by the manufacturer of a membrane module following extensive testing of a number of membrane modules of a given type. In whatever way 111–113 reference signal 110 is provided, reference signal 110 is then compared at 86 with an echo signal 114 that is provided by a sensing transducer 79, such as shown in FIGS. 7 and 8.

FIG. 16 shows another type of multiple reflecting layer membrane module 120 with which the present invention finds utility. Membrane module 120 includes a generally flat top metal plate 121, and a generally flat bottom metal plate 122. Feed liquid enters module 120 and its internal area 126 at 123, the feed liquid being under pressure. Retentate exits module area 126 at 124. A multi-layer membrane area 125 is supported by bottom plate 122. Membrane area 125 includes a relatively large number of alternating membrane layers 127 and porous support layers 128. As shown at 129, permeate exits porous support layers 128; for example, to the left side of module 120.

Using any of the means above described, a sensing transducer 70 is pulse-energized to interrogate the state of fouling, or the state of cleaning, of membrane area 125, and an echo signal 76 is compared to a reference in order to determine the state of fouling, or the state of cleaning, of membrane area 125.

In accordance with the spirit and scope of this invention, the above-described step of comparing a membrane echo signal to a reference echo signal may comprise comparing amplitude domain signals, comparing time-domain signals, comparing combinations of amplitude-domain and time-domain signals, and/or comparing transformations of amplitude-domain and time-domain signals. A non-limiting example of such a transformation is the transformation of a time-domain signal into a frequency-domain signal. In providing such a time-domain to frequency-domain transformation, Fast Fourier Transform (FFT) software may be used.

In addition, while embodiments of the invention that are exemplified by FIG. 7 are usable in the field by attaching the above-described ultrasonic transducer to a membrane module, embodiments of the invention, such as are exemplified by FIG. 8, allow the above-described ultrasonic transducer to be mounted on the outer surface of a membrane module as a part of the initial manufacture of the membrane module.

This invention operates to consider the response of multiple membrane layers to a transmitted pulse, and the multiple echo scatters that result therefrom.

Operation of this invention obtains an envelope function, a descriptor, or an index for the complete time-domain echo response (or for a frequency-domain echo response that is obtained from the time-domain echo response) from the ensemble of echo scatters.

Such a time-domain echo signal comprises an echo signal assembly having an ensemble of echo scatters that are obtained from the multiple layers of a spiral-wound membrane, or from the multiple surfaces of the hollow fibers within a hollow fiber membrane.

This envelope function, descriptor, or index (which is a function of time) is then compared to a reference signal (for example, to a reference signal that is obtained from a transducer that interrogates the membrane at a location that is known to be associated with no fouling), or with very little fouling, as the membrane is used in a liquid separation process, an example being a reference portion of the membrane that is adjacent to the feed inlet.

In a simple multiple scattering system, the log decrement that is obtained from the processed time-domain signal changes as a function of membrane fouling. The magnitude and the separation of peaks in the frequency-domain (spectrum) change for multiple layers, as the layers foul.

For a general tutorial, see Structure Analysis by Scattered Ultrasonic Radiation by K. Goebbels (*Research Techniques in NDT,* Chapter 4, Vol. 4, Ed. R. S. Sharpe, Academic Press, 1981), wherein it is stated that for a fixed position of a probe and a sample, the single high-frequency backscatter signal (A-scan) represents an interference pattern as a result of superimposing all scattering processes from all of the scatterers (such as the grains in a polycrystalline material) which lie in the probe-transmitted sound beam, and that the amplitude modulated backscatter signal has a frequency spectrum that is quite similar to the spectrum of the transmitted signal.

While the above-describe embodiments of this invention have been described with reference to ultrasonic transducers that are mounted relative to the outside surface of a membrane module, it is within the spirit and scope of this invention to manufacture membrane modules with one or more ultrasonic transducers integral with either the outer surface or the inner surface of the module's external high pressure housing.

What is claimed is:

1. A method of monitoring a state of fouling of a membrane that is contained within a housing of a spiral wound or a hollow fiber membrane module, said housing having an outer surface, comprising the steps of:
   providing an ultrasonic transducer having an emitting face;
   positioning said transducer with said emitting face in physical engagement with said outer surface;
   pulse energizing said transducer;
   detecting a membrane echo signal that results from said pulse energization of said transducer;
   providing a reference echo signal that is indicative of an unfouled state of said membrane or of a fouled state of said membrane;
   comparing said membrane echo signal to said reference echo signal; and
   determining said state of fouling of said membrane based upon said comparing step.

2. The method of claim 1 wherein said step of comparing said membrane echo signal to said reference echo signal is selected from the group, comparing amplitude-domain signals, comparing time-domain signals, comparing combinations of amplitude-domain and time-domain signals, and comparing transformations of amplitude domain and time-domain signals.

3. The method of claim 1 wherein said step of positioning said ultrasonic transducer with said emitting face in physical engagement with said outer surface comprises the step of:
   physically mounting said ultrasonic transducer on said outer surface during manufacture of said membrane module.

4. The method of claim 3 wherein said membrane echo signal and said reference echo signal are selected from the group amplitude-domain signals, time-domain signals, combinations of amplitude domain and timedomain signals, and transformations of amplitude domain and time-domain signals.

5. The method of claim 1 including the steps of:
   providing said ultrasonic transducer as a focused ultrasonic transducer having a focal length of about 4-inches and having an emitting face formed as a portion of a circular cylinder having a radius of curvature of about 3-inches;
   providing said membrane module as a circular cylinder membrane module having an outer high-pressure housing having a diameter of about 3-inches; and
   providing said pulse energization of said transducer as alternating current pulse energization in the range of from about 0.5 MHz to about 5 MHz.

6. The method of claim 5 wherein said pulse energization of said transducer is provided at about 3 MHz.

7. The method of claim 6 wherein said membrane echo signal and said reference echo signal are selected from the group amplitude domain signals, time-domain signals, combinations hereof, and transformations thereof.

8. The method of claim 7 wherein said emitting face is about 0.75 inch in diameter.

9. A method of monitoring a cleaning process by which a fouled membrane is cleaned, the membrane being selected from the group hollow fiber membrane and spiral-wound membrane, and said membrane being contained within a housing having an outer surface, comprising the steps of:
   providing an ultrasonic transducer having a face surface;
   positioning said transducer on said outer surface with said face surface in physical engagement with said outer surface;
   starting said cleaning process;
   pulse energizing said transducer;
   detecting a membrane echo signal that is produced by said pulse energization of said transducer;
   providing a reference echo signal that is indicative of a clean state of said membrane, or alternatively providing a reference echo signal that is indicative of a fouled state of said membrane;
   comparing said membrane echo signal to said a reference echo signal;
   determining a state of cleaning of said membrane based upon said comparing step; and
   terminating said cleaning process as a function of said determining step.

10. The method of claim 9 wherein said comparing step is selected from the group time domain comparing step, amplitude-domain comparing step, combinations of time-domain and amplitude domain comparing step, and transformations of time-domain and amplitude domain comparing step.

11. The method of claim 10 including the steps of:
    providing said ultrasonic transducer as a focused ultrasonic transducer having a focal length of about 4-inches and having an emitting face formed as a portion of a circular cylinder having a radius of curvature of about 3-inches;
    providing said membrane module as a circular cylinder membrane module having an outer high pressure housing having a diameter of about 3-inches; and
    providing said pulse energization of said transducer as alternating current pulse energization in the range of from about 0.5 MHz to about 5 MHz.

12. The method of claim 11 wherein said pulse energization of said transducer is provided at about 3 MHz.

13. The method of claim 12 wherein said face surface of said transducer is about 1 inch in diameter.

14. A method of monitoring a state of fouling of membranes in a multi-layer configuration, comprising the steps of:

provomg a membrane module having a housing with an outer surface, having said multi-layer membrane configuration contained within said housing, having a feed inlet, having a permeate outlet, and having a retentate outlet;

providing a first and a second ultrasonic transducer, each of said transducers having a face surface that generally corresponds to said outer surface of said housing;

positioning said first transducer on said outer surface of said housing general adjacent to said feed inlet and with said face surface in physical engagement with said outer surface;

positioning said second transducer on said outer surface of said housing general adjacent to said retentate outlet and with said face surface in physical engagement with said outer surface;

pulse energizing said first and second transducers;

detecting a first and a second membrane echo signal that are respectively produced by said pulse energization of said first and second transducers;

said first membrane echo signal being indicative of membrane fouling generally adjacent to said feed inlet;

said second membrane echo signal being indicative of membrane fouling generally adjacent to said retentate outlet;

comparing said first membrane echo signal to said second membrane echo signal; and determining said state of fouling of said multi-layer membrane configuration based upon said comparing step.

15. The method of claim 14 wherein said multi-layer membrane configuration is selected from the group hollow fiber membrane and spiral-wound membrane.

16. The method of claim 14 wherein said comparing step is a time domain and/or amplitude domain comparing step.

17. The method of claim 14 wherein said comparing step operates to compare time-domain signals, and/or amplitude domain signals, and/or combinations of time-domain and amplitude domain signals, and/or transformations of time-domain signals, and/or transformations of amplitude domain signals.

18. The method of claim 14 wherein said step of positioning said first and second ultrasonic transducers with said face surfaces in physical engagement with said outer surface of said housing comprises the step of:

physically mounting said first and second ultrasonic transducers on said membrane module during manufacture of said membrane module.

19. The method of claim 14 including the steps of:

providing said first and second ultrasonic transducers as focused ultrasonic transducers, each having a focal length of about 4-inches and each having a face surface that is formed as a portion of a circular cylinder having a diameter of about 3-inches;

providing said membrane module as a circular cylinder membrane module having an outer high pressure housing having a diameter of about 3-inches; and providing said pulse energization of said first and second transducers as alternating current pulse energization at about 0.5 MHz to about 5 MHz.

20. The method of claim 19 wherein said pulse energization of said first and second transducers occurs at about 3 MHz.

21. The method of claim 20 wherein said face surface of each of said first and second transducers is about 1-inch in diameter.

22. The method of claim 14 wherein said method is practiced during use of said membrane module in a liquid separation process wherein liquid feed enters said membrane module by way of said feed inlet, wherein a first liquid component exits said membrane module by way of said permeate outlet, and wherein a second liquid component exits said membrane module by way of said retentate outlet.

23. The method of claim 14 wherein said method is practiced during cleaning of said membrane module wherein a liquid is provided in said membrane.

24. Apparatus for determining the state of fouling of a liquid separation membrane that is contained within a housing having an outer surface, having a liquid feed inlet, having a permeate liquid outlet that is physically spaced from said liquid feed inlet by said membrane, and having a retentate liquid outlet that is physically spaced from said liquid feed inlet and generally comprises an extension of said liquid feed inlet, said apparatus comprising:

at least one sensing ultrasonic transducer mounted on said housing generally adjacent to said permeate liquid outlet, said at least one transducer having a wave energy emitting/receiving face surface whose shape physically complements said outer surface of said housing;

sensing pulser/receiver means connected to said at least one transducer and operable to cause said at least one transducer to operate in a pulse/echo mode of operation wherein for each pulse energization of said at least one transducer by a pulse portion of said sensing pulser/receiver means a wave of energy is transmitted through said housing and into said membrane, and an echo wave of energy is thereafter received by said at least one transducer, said echo wave of energy being converted to an electrical signal by said at least one transducer, and said electrical signal then being processed by a receiver portion of said sensing pulser/receiver means;

an electrical source providing a reference signal indicative of a reference state of fouling of said membrane;

comparison means having a first input connected to receive said processed electrical signal from said receiver portion of said sensing pulser/receiver means, having a second input connected to receive said reference signal, and having an output;

a threshold signal source operable with said comparison means and defining a predetermined state of fouling of said membrane; such that when said apparatus is used to monitor a state of fouling of said membrane module as a liquid is being separated, said output provides a signal indicative of a need to clean said membrane module; and such that when said apparatus is used to monitor a state of fouling of said membrane module as said membrane module is being cleaned, said output provides a signal indicative of termination of said membrane module cleaning.

25. The apparatus of claim 24 wherein:

said electrical source providing said reference signal includes a reference ultrasonic transducer that is mounted on or in said housing generally adjacent to said liquid feed inlet, said reference transducer having a wave energy emitting/receiving face surface whose shape complements said outer surface of said housing, and a reference pulser/receiver device operable with said reference transducer to provide said reference signal.

26. The apparatus of claim 25 wherein said liquid separation membrane is selected from the group spiral-wound membrane and hollow fiber membrane.

27. The apparatus of claim 24 wherein said housing comprises an elongated cylinder, with said liquid feed inlet being located generally at one end of said cylinder, and with said retentate outlet being located generally at an opposite end of said cylinder, said apparatus including:

a plurality of sensing ultrasonic transducers mounted at a plurality of spaced positions along a length of said cylinder, said plurality of sensing transducers being periodically connected to said sensing pulser/receive means so as to provide for the periodic sensing of membrane fouling at membrane positions generally corresponding to said plurality of spaced positions.

28. The apparatus of claim 27 wherein:

said electrical source providing said reference signal includes a reference ultrasonic transducer that is mounted on or in said housing generally adjacent to said liquid feed inlet, said reference transducer having a wave energy emitting/receiving face surface whose shape complements said outer surface of said housing, and a reference pulser/receiver device operable with said reference transducer to provide said reference signal.

29. The apparatus of claim 28 wherein said liquid separation membrane is selected from the group spiral-wound membrane and hollow fiber membrane.

30. The apparatus of claim 24 wherein said housing comprises an elongated cylinder with said liquid feed inlet being located generally at one end of said cylinder and with said retentate outlet being located generally at an opposite end of said cylinder, said apparatus including:

motor means operable to move said at least one transducer between spaced locations along a given length of said cylinder so as to provide for the sensing of membrane fouling along a membrane length generally corresponding to said given length of said cylinder.

31. The apparatus of claim 30 wherein:

said electrical source providing said reference signal includes a reference ultrasonic transducer that is mounted on or in said housing generally adjacent to said liquid feed inlet, said reference transducer having a wave energy emitting/receiving face surface whose shape complements said outer surface of said housing, and a reference pulser/receiver device operable with said reference transducer to provide said reference signal.

32. The apparatus of claim 31 wherein said liquid separation membrane is selected from the group spiral-wound membrane and hollow fiber membrane.

33. A method that determines fouling of a membrane utilized for liquid separation and that is contained within a housing having an outer surface, having a liquid feed inlet, having a permeate outlet that is physically spaced from said liquid feed inlet by said membrane, and having a retentate outlet that is physically spaced from said liquid feed inlet and is generally an extension of said liquid feed inlet, said method comprising the steps of:

providing at least one sensing ultrasonic transducer that is mounted on said outer surface of said housing generally adjacent to said retentate outlet, said at least one sensing transducer having a wave energy emitting/ receiving face surface whose shape complements said outer surface of said housing;

providing sensing pulser/receiver means connected to said at least one sensing transducer and operable to cause said at least one sensing transducer to operate in a pulse/echo mode wherein for each pulse energization of said at least one sensing transducer by a pulse portion of said sensing pulser/receiver means a wave of energy is transmitted through said housing and into said membrane, and to cause an echo wave of energy to be thereafter received by said at least one sensing transducer, said echo wave of energy being converted to an electrical signal by said at least one sensing transducer, and said electrical signal then being processed by a receiver portion of said sensing pulser/ receiver means;

providing an electrical source that provides a reference signal indicative of a reference state of fouling of said membrane;

providing comparison means having a first input connected to receive said processed electrical signal from said receiver portion of said sensing pulser/receiver means, having a second input connected to receive said reference signal, and having an output;

such that when said method is used to monitor a state of fouling of said membrane module as a feed liquid is being separated, said output provides a signal indicative of a need to clean said membrane module; and such that when said method is used to monitor a state of fouling of said membrane module as said membrane module is being cleaned, said output provides a signal indicative of the fact that said membrane module is clean.

34. The method of claim 33 wherein said membrane is selected from the group spiral-wound membrane and hollow fiber membrane.

35. The method of claim 33 including the steps of:

providing a reference ultrasonic transducer that is mounted on said outer surface of said housing generally adjacent to said liquid feed inlet, said reference transducer having a wave energy emitting/receiving face surface whose shape complements said outer surface of said housing; and providing a reference pulser/receiver device operable with said reference transducer to provide said reference signal.

36. The method of claim 35 wherein said membrane is selected from the group spiral-wound membrane and hollow fiber membrane.

37. The method of claim 33 wherein said housing comprises an elongated cylinder with said liquid feed inlet being located generally at one end of said cylinder and with said retentate outlet being located generally at an opposite end of said cylinder, said method including the step of:

providing a plurality of sensing ultrasonic transducers mounted on an outer surface of said cylinder and at a plurality of spaced positions along a length of said cylinder, said plurality of sensing transducers being connected to said sensing pulser/receive means so as to provide for the sensing of membrane fouling at membrane positions generally corresponding to said plurality of spaced positions.

38. The method of claim 37 including the steps of:

providing a reference ultrasonic transducer that is mounted on said outer surface of said cylinder generally adjacent to said liquid feed inlet, said reference transducer having a wave energy emitting/receiving face surface whose shape complements said outer surface of said cylinder; and providing a reference pulser/receiver device operable with said reference transducer to provide said reference signal.

39. The method of claim 38 wherein said membrane is selected from the group spiral-wound membrane and hollow fiber membrane.

40. The method of claim 33 wherein said housing comprises an elongated cylinder having said liquid feed inlet located generally at one end of said cylinder and having with said retentate outlet located generally at an opposite end of said cylinder, said method including the step of:

providing motor means operable to move said at least one sensing transducer between spaced locations along a given length of said cylinder so as to provide for the sensing of membrane fouling at a membrane length generally corresponding to said given length of said cylinder.

41. The method of claim 40 including the steps of:

providing a reference ultrasonic transducer mounted on an outer surface of said cylinder generally adjacent to said liquid feed inlet, said reference transducer having a curved wave energy emitting/receiving face that complements said outer surface of said cylinder; and providing a reference pulser/receiver device operable with said reference transducer to provide said reference signal.

42. The method of claim 41 wherein said membrane is selected from the group spiral-wound membrane and hollow fiber membrane.

43. A method of determining a state of fouling of a polymeric membrane that is contained within a housing of a spiral-wound membrane module or a hollow fiber membrane module, comprising the steps of:

positioning a sensing ultrasonic transducer with an emitting/receiving face in physical engagement with an outer surface of said housing;

electrically connected said sensing transducer to an ultrasonic pulser/receiver device;

pulse energizing said sensing transducer by operation of a pulser portion of the pulser/receiver device;

detecting a membrane echo signal by operation of a receiver portion of said pulser/receiver device;

providing a reference echo signal that is indicative of an predetermined state of membrane fouling; and determining a state of fouling of said membrane based upon a comparison of said membrane echo signal to said reference echo signal.

44. The method of claim 43 wherein said determining step comprises the step of comparing a characteristic of said membrane echo signal to a similar characteristic of said reference echo signal.

45. The method of claim 44 wherein said characteristic is selected from the group an amplitude characteristic, a time characteristic, combinations of an amplitude characteristic and a time characteristic, a transformation of an amplitude characteristic, and a transformation of a time characteristic.

46. The method of claim 43 including the step of:

providing said reference echo signal by the operation of a reference ultrasonic transducer that provides a membrane echo signal that is derived from an area of said membrane that is known to remain relatively unfouled during a liquid separation process.

47. The method of claim 43 including the step of:

providing a plurality of sensing transducers;

locating said plurality of sensing transducers at a plurality of physically spaced locations on said outer surface of said housing;

sequentially pulse energizing said plurality of sensing transducers by operation of said pulser portion of the pulser/receiver device and detecting a plurality of membrane echo signals that are thereby produced by operation of said receiver portion of said pulser/receiver device; and determining a state of fouling of said membrane based upon a plurality of comparisons of said plurality of membrane echo signals to said reference echo signal.

48. The method of claim 47 including the step of:

providing said reference echo signal by the operation of a reference ultrasonic transducer that provides a membrane echo signal that is derived from an area of said membrane that is known to remain relatively unfouled during a liquid separation process.

49. The method of claim 48 wherein said determining step comprises the step of comparing a characteristic of said plurality of membrane echo signals to a similar characteristic of said reference echo signal.

50. The method of claim 49 wherein said characteristic is selected from the group amplitude characteristic, time characteristic combinations of amplitude characteristic and time characteristic, transformation of amplitude characteristic, and a transformation of time characteristic.

* * * * *